United States Patent
Helfmann et al.

(10) Patent No.: US 10,132,748 B2
(45) Date of Patent: Nov. 20, 2018

(54) SENSOR DEVICE FOR HIGH-RESOLUTION DETECTION OF TARGET SUBSTANCES

(71) Applicant: LASER—UND MEDIZIN-TECHNOLOGIE GMBH BERLIN, Berlin (DE)

(72) Inventors: Jürgen Helfmann, Klein-Machnow (DE); Hans-Joachim Cappius, Berlin (DE)

(73) Assignee: Courage + Khazaka electronic GmbH, Köln (DE)

( * ) Notice: Subject to any disclaimer, the term of this patent is extended or adjusted under 35 U.S.C. 154(b) by 0 days.

(21) Appl. No.: 15/123,894

(22) PCT Filed: Mar. 6, 2015

(86) PCT No.: PCT/EP2015/054795
§ 371 (c)(1),
(2) Date: Sep. 6, 2016

(87) PCT Pub. No.: WO2015/132412
PCT Pub. Date: Sep. 11, 2015

(65) Prior Publication Data
US 2017/0108433 A1 Apr. 20, 2017

(30) Foreign Application Priority Data
Mar. 7, 2014 (DE) .................. 10 2014 003 470

(51) Int. Cl.
*G01N 21/00* (2006.01)
*G01N 21/47* (2006.01)
(Continued)

(52) U.S. Cl.
CPC ....... *G01N 21/4785* (2013.01); *A61B 5/1455* (2013.01); *A61B 5/14535* (2013.01);
(Continued)

(58) Field of Classification Search
CPC ............ G01N 21/53; G01N 21/538; G01N 2021/4709; G01N 15/0205; G01N 21/21
(Continued)

(56) References Cited

U.S. PATENT DOCUMENTS 7,139,076 B1 11/2006 Marbach
8,604,436 B1 * 12/2013 Patel .................. H01L 25/50
250/338.1
(Continued)

FOREIGN PATENT DOCUMENTS

DE 102007054309 A1 5/2009
EP 0760091 B1 11/1999
(Continued)

OTHER PUBLICATIONS

International Search Report issued by the European Patent Office in International Application PCT/EP2015/054795.

*Primary Examiner* — Md M Rahman
(74) *Attorney, Agent, or Firm* — Henry M. Feiereisen LLC

(57) ABSTRACT

An optical sensor device which measures in a spatially resolving manner is disclosed. In order to devise such a sensor device with which a contacting measurement of the article to be measured can be carried out and which can be mass-produced, the sensor device is designed such that a transfer of the calibration onto individual sensor devices is possible with high accuracy. According to certain embodiments of the design of the sensor device and of the evaluation methods, interferences with the measurement of the amount of the target substance are minimized.

16 Claims, 8 Drawing Sheets

(51) Int. Cl.

| | |
|---|---|
| *G01J 3/02* | (2006.01) |
| *G01J 3/42* | (2006.01) |
| *G01N 21/3554* | (2014.01) |
| *G01N 21/49* | (2006.01) |
| *A61B 5/145* | (2006.01) |
| *A61B 5/1455* | (2006.01) |
| *G01J 3/10* | (2006.01) |
| *G01N 21/33* | (2006.01) |
| *G01N 21/31* | (2006.01) |

(52) U.S. Cl.
CPC ........ *A61B 5/14546* (2013.01); *G01J 3/0218* (2013.01); *G01J 3/0262* (2013.01); *G01J 3/0286* (2013.01); *G01J 3/0291* (2013.01); *G01J 3/0294* (2013.01); *G01J 3/0297* (2013.01); *G01J 3/42* (2013.01); *G01N 21/3554* (2013.01); *G01N 21/49* (2013.01); *G01J 2003/104* (2013.01); *G01N 21/33* (2013.01); *G01N 2021/3144* (2013.01); *G01N 2021/4709* (2013.01); *G01N 2021/4733* (2013.01); *G01N 2201/1211* (2013.01)

(58) Field of Classification Search
USPC .......................................................... 356/342
See application file for complete search history.

(56) References Cited

U.S. PATENT DOCUMENTS

| | | | |
|---|---|---|---|
| 2002/0120203 | A1 | 8/2002 | Higurashi |
| 2010/0290032 | A1* | 11/2010 | Bugge .................... B07C 5/342 356/51 |
| 2012/0002035 | A1* | 1/2012 | Li .......................... F01D 17/085 348/82 |
| 2012/0026319 | A1* | 2/2012 | Hsu .................... G01B 11/2518 348/135 |
| 2013/0144139 | A1* | 6/2013 | Zhang ................ A61B 5/14525 600/322 |

FOREIGN PATENT DOCUMENTS

| | | |
|---|---|---|
| EP | 0756 848 A1 | 5/2009 |
| WO | WO2013/049677 A1 | 4/2013 |

* cited by examiner

A-A

SENSOR DEVICE FOR HIGH-RESOLUTION DETECTION OF TARGET SUBSTANCES

CROSS-REFERENCES TO RELATED APPLICATIONS

This application is the U.S. National Stage of International Application No. PCT/EP2015/054795, filed Mar. 6, 2015, which designated the United States and has been published as International Publication No. WO 2015/132412 and which claims the priority of German Patent Application, Serial No. 10 2014 003 470.4, filed Mar. 7, 2014, pursuant to 35 U.S.C. 119(a)-(d).

BACKGROUND OF THE INVENTION

Object

It is an object to provide a mass producible sensitive spatial resolution sensor for determining substance amounts in different depth of biological tissues and other opaque substance mixtures by way of their spectral signature. The detection is to be accomplished through direct contact between a spatially resolving sensor and the biological tissue or substance mixtures, wherein a high sensitivity of the sensor is desired. A challenge hereby is to accurately determine the amount of the target substance when other substances vary.

State of the Art

The determination of a concentration of a substance to be determined can be accomplished via the absorption of the substance $\mu a = c \cdot epsilon$, wherein $\mu a$ is the absorption coefficient, c the concentration and epsilon the molar extinction. The diffuse reflection detected in the spatially resolved measurement in case of opaque (scattering) substance mixtures however depends on the absorption coefficient $\mu a$ and on the scattering coefficient $\mu s$. Thus for example the entire backscatter depends on the ratio $\mu s/\mu a$ (scattering and absorption). This means that the measurement of an individual backscatter signal does not allow to unequivocally determine the absorption coefficient and with this the concentration of the target substance. Instead multiple independent backscatter signals have to be determined in order to enable a separation of absorption and scattering or in the case of a varying scatter coefficient of the substance mixture to determine an unequivocal concentration of a given substance. According to the invention these are determined by measuring the reflectance (backscatter) in multiple different distances from the spatially limited radiation source. By analyzing multiple backscatter signals $\mu s$ and $\mu a$ can principally be determined independent of each other.

This method is known from the state of the art as "spatially resolved reflectance (SRR). Not known however is the advantageous configuration of the device and method according to the invention. These are intended to be protected in this application.

SUMMARY OF THE INVENTION

Description of the Invention

The sensor according to the invention is to be configured for mass production so that the calibration of one pre-calibrated sensor can be applied with high accuracy to a multitude of other similarly constructed sensors. This involves taking aspects of the sensor design and the analysis methods into account. First the aspects of the sensor design are described that are relevant for a highly sensitive and reproducible measurement, then the aspects of the (measurement) analysis are described and finally aspects that are advantageous for a mass production and aspects of the simple application of a calibration to individual sensor units are described.

From DE 10 2007 054 309 it is known that the distance between a radiation input site and a site of detection in a strongly scattering medium i.e., in a medium whose scatter coefficient $\mu s$ is much greater than the absorption coefficient $\mu a$ and the product of the thickness d and $\mu s$ is much greater than 1, influences the size of the irradiated volume. The path length of the radiation s increases hereby approximately linearly with the distance d (R. A. Bolt, K. R. Rinzema, J. J. ten Bosch, Pure Appl. Opt. 4, 1995). In case of a small absorption the extension of the path s/d 4.5. This allows mostly detecting those portions of the radiation that emerge from the depth of the substrate to the surface again at same distance due to scattering.

The radiation distribution can be approximately determined by a diffusion approximation of the radiative transport equation in dependence on the distance d of the locations for the irradiation and detection approximately (S. Feng, F.-A. Zeng, B Chance, Appl. Opt. Vol 34 No 19, 1995). For the radiation propagation the damping coefficient $\mu eff$ results from $$\mu eff = (3ma(\mu a + \mu s(1-g)))^{1/2}$$

wherein $\mu s$ is the scatter coefficient and g as the mean cosine of the scatter describes the propagation direction of the radiation.

The depth at which the maximum of the detected radiation distribution is located can be approximately determined as:

$$zmax = (d/(2\mu eff))^{1/2}$$

According to the invention the substance to be determined can thus be determined from measurements at a predetermined depth zmaz by constructing the sensor with a distance d between the site of radiation input and radiation detection, which distance is derived from zmax. The goal is thus to maximize the light distribution in the target volume in which the concentration of the substance to be quantified is to be determined.

The spatial extent of the measuring volume extends as a banana shaped volume from the surface of the measuring object from the site of radiation input to the site of detection, so that for a reliable quantification also the portions of the layers that are situated above the target volume have to be detected to allow those portions to be cancelled out. In homogenous media the maximal depth of the light propagation is situated approximately between the site of radiation input and the site of radiation detection.

The sensor according to the invention thus has multiple radiation sources and multiple detectors located at different distances d to each other, which provide different measurement values, which enable detection of different target volumes, wherein the target volumes at least partially overlap each other.

An advantageous additional feature of the alternative for determining the volumes through which the radiation passes is the simulation of the propagation of the radiation in the measuring object for example by the known Monte Carlo simulation. For this purpose however assumptions regarding the optical properties $\mu a$, $\mu s$ and g prevailing in the measuring object have to be made. The assumptions of $\mu s$ and g can be replaced in the formula µs'=µs·(1−g) also by the assumption of the reduced scatter coefficient µs'.

According to an advantageous embodiment the determination of the light distribution via the distances between the radiation source and the detector(s) (sites of radiation input and detection sites) can be used for depth weighting of the concentration determination for example in order to correct in layer systems for each layer concentrations or surface effects or effects caused by deeper layers.

Preferably the desired or required path length in the tissue is selected by optimizing the signal intensity that can minimally be detected with the sensor, which is proportional to $e^{-factor*wavelength*absorption\ at\ the\ selected\ wavelength}$, in dependence on the maximally admissible radiation intensity, so that the path length for long paths results in a sensitive detection but also a small signal. Hereby the term factor means the light path extension in the measuring object, factor*path length thus defines the optical path length. The goal is thus to determine the absorption of the measuring object for the wavelengths defined by the target substance (see further below for selecting the wavelengths) and to determine the minimal signal intensity at the detector so that a longest possible path length can be used for the greatest distance d between the radiation source and the detector.

In homogenous media it is therefore not important to take the measuring depth achieved hereby into account, in layer systems the position of the target volume is also a limiting circumstance.

The detectors can be arranged at the same distance or at a different distance to each other. In a particularly advantageous arrangement the detectors are situated at an increasing distance to each other with increasing distance to the radiation source. This arrangement of the detectors relative to each other does not have to be along a straight line but can be arbitrary, also ring shaped or star shaped.

Long radiation paths in absorbing or scattering measuring objects cause a decrease of the amounts of radiation impinging on the detection site. Thus an increase of the detected signal by using multiple detectors, which can be arbitrarily arranged, with the same distance to the radiation input site, or also the increase of the detector surface in the sensor is advantageous. This includes the use of ring-shaped detectors as well as the use of multiple components, which are arranged adjacent each other.

The sensor is advantageously designed so that the light portions on the detectors, which are arranged at different distances, are differentially amplified to obtain same signal amplitudes. In particular the amplification of radiation amounts expected based on tests or simulations are preferably adjusted for each detector individually.

The wavelengths are selected in accordance with the target substance or target substances, preferably so that at least one respective wavelength or a wavelength range is used in which the sensor signals show clear effects on the radiation amounts detected by the detector or detectors for the target substance to be determined. In addition, for detecting interfering substances or other interfering influences at least one wavelength or a wavelength range is to be used in which one or more target substances show very small or no effects on the sensor signals, i.e., the radiation amounts detected by the detector or detectors. Thus preferably always at least one pair of wavelengths of the radiation, one of which shows an effect and one of which shows no effect, is radiated in at the distance d, which defines the target volume. The wavelengths that do not show an effect on the sensor signals can be the same for multiple target substances and serve for suppressing the interference. The use of more than one wavelength per target substance that shows an effect on the sensor signals advantageously increases the accuracy and with this the smallest quantifiable concentration of the target substance in the target volume.

These wavelengths can be radiated in sequentially and can be simultaneously received by broadband detectors at different distances d.

The Lock-In-Technique described below can also be used in order to individually impinge each wavelength with a different frequency and in this way operate the LED continuously (not sequentially) and to filter the individual wavelength out again with broadband detectors by spectral frequency analysis or by sequential demodulation with the respective frequency.

It is also advantageous to use spectrally resolving detectors that make it possible to simultaneously irradiate with many wavelengths, for example by using a white light source as well as an incandescent light bulb or a white light LED.

The use of a component (reference detector) that detects the radiation emission of the radiation source without interacting with other substances is also advantageous. This reference detector can be placed directly adjacent the radiation source but can also detect the intensity of the radiation source via components that redirect portions of the radiation.

In order to be able to correct the temperature dependence of the radiation sources and measuring and reference detectors it is advantageous to conduct a portion of the radiation emission of the radiation source to the reference detector thereby detecting this portion.

In order to minimize the influence of the temperature on this reflectance based transmission the temperature dependence of the reflectivity under 90 was investigate for different surfaces.

| Material/component | Surface processing | Change of reflexivity at ΔT = 25K in % remission |
| --- | --- | --- |
| POM black | milled | 2.9 |
| POM white | milled | 0.7 |
| PTFE white | turned | 0.6 |
| Spectralon/Reflectance standard | | 0.0 |
| Aluminum alloy | milled | 0.4 |
| Aluminum alloy | Milled, black anodized | 1.7 |
| Aluminum alloy of the sensor carrier | Milled, black anodized | 15.5 |
| AlN-ceramic | | 0.0 |

Change of reflexivity at heating from 20° C. by 25K

Advantageously thus Spectralon, AlN-ceramic or blank milled aluminum alloy should be used for the deflection of radiation to the reference detector.

In order to stabilize the radiation output of the radiation source the use of a constant current source or stabilized voltage supply is advantageous. Another refinement in accordance with the invention involves the use of a lock-in technique with pulsed or sinusoid emitted intensity and correspondingly a frequency at the intensity, which is adjusted to interferences as described below or with higher pulse rate readout detectors is possible.

It is not required to adhere to exactly defined distances between the radiation source and the detector(s) but smaller deviations and expansions within the usual placement accuracy in the case of small dimensioned components, that are for example mounted as a chip, i.e., components without a housing, do not have a significant influence on the accurate determination of the amounts of the target substance when mastering the remaining advantageous measures that are taken in the case of strongly scattering measuring objects. The admissible smaller deviations, i.e., the tolerance is linearly related to the distance x at which the radiation has fallen to 1/e and to the accuracy with which the target substance is sought to be determined; the tolerance is to be smaller than x/n, wherein n is defined by the desired accuracy of the concentration of the target substance.

The use of components without housing for the radiation sources enables a compact placement of multiple sources on a small surface so as to realize without radiation forming elements a single radiation input site for multiple freely selectable wavelengths on the measuring object. Using components as radiation source that do not have housing also enables a placement of the components at small distances and introduction of uniform, overlapping light distribution on the measuring object (radiation input site) and to detect the light distribution with high spatial resolution.

Also the use of small, housed components, which for example includes groups of LEDs or photodiodes or both or similar radiation sources and/or detectors, is preferred.

Thus a sensor design with adjacently arranged illumination components, i.e., radiation sources and detector components arranged at a distance d therefrom (for example relative to the center of the components), i.e., radiation detectors, is possible and preferred.

Also advantageous and preferred is the use of similar components for the detectors at all distances. In this case the component properties such as temperature-dependencies are similar and can thus be corrected more easily.

According to another feature of the invention the use of non-linear or algorithmic amplification devices is preferred. These non-linear or algorithmic amplification devices can bring the signals generated at the detectors to same signal amplitudes by stronger amplification of the weaker signals relative to the detectors that are situated closer to the radiation input site, which is advantageous for the further processing, digitalization or analysis.

According to another feature of the invention the sensor is produced as a module, which can be installed like an electronic component in devices, with at least one LED and at least one photodiode in a cast housing. It is also advantageous when the control electronics and the pre-amplifiers are integrated in the module. Also only LEDs or photodiodes may be used in a module for the sensor.

It is also advantageous to correct the temperature dependency of the radiation source and the detector with a known temperature characteristic or temperature measurement.

FIG. 1 shows an exemplary embodiment in which four photodiodes (PD) and six LEDs as radiation sources and a monitoring photodiode as reference detector are cast in at specific distances to each other and their contacts are guided outwardly, wherein the designation LED may also stand for another radiation source and PD also for another detector. The numbers designate the connections (pins) counted through and guided outwardly, the components are electrically connected by means of bonding or similar techniques according to the state of the art. Without limiting the invention the distances and wavelengths or the general outer shape of the module, the shape and the location of radiation barriers and other aspects mentioned in this document can be adjusted corresponding to the design directives mentioned in this document or according to the state of the art.

According to another feature of the invention it is also possible to design modules or assembly groups exchangeable with interfaces so that in during assembly of a device, the modules or assembly groups can be easily exchanged. This enables replacement of defective assembly groups and also a simple adjustment to different target volumes (measuring depth) by exchanging detector groups with differing distances, as well as adjustment to other target substances or also a different medium by exchanging the assembly groups with the radiation source or radiation sources.

According to another feature of the invention, it is also possible to alter the sequence of the photodiodes and radiation sources so that radiation sources have a short distance to a neighboring detector and a different greater distance to another detector. Adjacent the detector for the first radiation source placed at a greater distance a further radiation soured can be placed, which in switching of the detectors has similar distances for the analysis, and thus represents a second wavelength with similar distances in inverted order, wherein in the analysis the detectors are also assigned in inverted order. This nested arrangement enables a space saving construction of such a sensor. An example of the construction of such an arrangement is shown in FIG. 2. Without limiting the invention other, also asymmetric arrangements and also arrangements with a different number of components or without temperature sensor are within the scope of the invention.

According to another feature of the invention the construction of the sensor can also be changed in that the exit and entry location of the radiation is separated from the location of the components. Thus the sensor construction can be geometrically decoupled, preferably by a transmission optics between the radiation source and the entry window for example by a glass fiber or a glass rod with at least one prism or similar beam conductions corresponding to the state of the art, while remaining optically coupled by the beam conduction.

According to another feature of the invention, the sensor can measure while being in direct contact with the measuring object, or a purely optical coupling to the measuring object by projecting of light sources and detectors on the measuring object by lens systems or similar devices or a mechanical and optical coupling to the measuring object is provided. This is further explained by way of FIG. 3, wherein the designation LED can stand for a radiation source (also other than LED) and PD for a detector (also other than a photo diode):

Generally the sensor according to the invention faces the task to locally illuminate a sample surface with a radiation source which sample surface is situated at a defined distance and to detect the distance-dependent remission in a spatially resolved manner. Hereby it is desirable to achieve a sufficient field depth of the projection, which however is in reciprocal relationship (NA↑⇨ field depth↓) with the achievable light throughput (which is defined by the NA (numerical aperture)). Advantageous is the use of a spacer, which enables accurately maintaining the distance between the sensor and the measuring object. Also advantageous is a different method is a different method for determining the distance, which can then advantageously be held constant by automatic processes.

One of the possible solutions is a common collector lens for the radiation source and the detectors (FIG. 3 solution A): this solution is not practicable because the photodiodes would be directly irradiated via the reflection on the glass surface.

When using two separate collector lenses (FIG. 3 solution B) with radiation barrier placed there between a common projection is achieved but the dimension is relative great.

The requirement of small distances (these are the spatial resolutions multiplied by the magnification ratio or reduction ratio) results in the requirement of small lens diameters that only have a small NA.

In order to address this problem one could tilt the radiation paths relative to each other with 2 separate collector lenses (FIG. 3 solution C). This results in the problem that the measurement at the predetermined distance of illumination to the detection locations can only be accomplished in that the correct distance of the sensor to the sample surface because the distance of the irradiation and the detection spots depends on the distance to the surface, i.e., the analysis is potentially not comprehensible. In addition the tilting results in the possible problem regarding the projection plane, which is tilted relative to the plane of the photodiodes. This requires a greater field depth or a special tilting of one of the plates.

When using a mirror or a prism in order to angle one of the radiation paths by 90 (FIG. 3 solution D), the irradiation and detection spots get closer to each other but there is still a relative great distance (several mm) between the irradiation and the detection at the level of the lens plane.

In addition the radiation paths could be tilted relative to each other (FIG. 3 solution E), which however causes the problems mentioned with regard to solution C in FIG. 3.

A different situation results when using GRIN lenses (FIG. 3 solution F). However this limits the distance of the lens surface to the sample to a few mm because the GRIN lenses only have small focal lengths. Moreover, the optical configuration is very inaccurate because an adjustment is accomplished by changing the length of the GRIN lenses. This results in higher demands on the manufacture of the fitting GRIN lenses, which have to be ground to length and subsequently polished. However GRIN lenses with a typically great NA are suited to advantageously collect a large portion of remitted light.

Also a combination of GRIN and collector lens (FIG. 3 solution G), i.e., to guide the illumination is conducted through the GRIN lens, still has the limitation of the proximity of the sample surface and the laborious manufacturing.

The use of thick fibers, i.e., glass rods which may also have rounded end surfaces (FIG. 3 solution H) would only result in a convergence of optical output or input regions and at the same time a spread out arrangement of the LED or photodiodes, the NA as well as the light throughput remains small. In addition the manufacturing costs of such specially formed glass rods are high.

The use of a hollow mirror (FIG. 3 solution I), which could be used off-axis, i.e., tilted and laterally irradiated is in accordance with the invention. The illumination-LED must not shine over the mirror, the NA is limited to 0.2 but due to insufficient focusing quality this application is limited to greater distances between light source/detector. There is no reflex of the LED from the mirror surface to the photodiodes because this could only be caused by scattering. The hollow mirror surface therefore has to be polished very well and no dust must adhere to it.

Another idea is to provide the hollow mirror with a hole through which the LED radiates off and which functions as an aperture (FIG. 3 solution J). In this case a focusing optics has to be additionally provided for the LED.

However in all the above solutions the direct reflectance of the illumination on the sample surface into the photodiodes cannot be excluded. This is the case in the pattern-free variant, i.e., 2 separate windows with radiation barrier in contact with the sample (FIG. 3 solution K) where also the NA of almost 1 represents the maximally realizable state. This is also possible in the case of separated optics (GRIN, fibers, rods, lenses) when a radiation barrier can be built in.

Also in accordance with the invention is the goal of a contact less measuring with a minimum distance. According to another feature of the invention a hollow mirror which is oriented perpendicular to the sample surface can be used in which a plate is mounted in the direction of the optical axis by means of a wire or a similar not strongly radiation absorbing device (FIG. 3 solution L), the LED carries. Hereby the borders are blackened so that no LED light can be reflected back or shines over.

According to another feature of the invention a mounting of the measuring object with a radiation output and input that is arranged in a definite manner with regard to the measuring object. This can be a mount for a tube-conducted medium whose inner diameter corresponds well to the outer diameter of the tube. According to the invention a parallel radiation path (reference branch) without medium can be used for a correction—for this possibility of the correction see further below the description of the measuring procedure. It is advantageous to configure the parallel radiation path so that another tube diameter can be held at this location and by changing the analysis i.e., the switching of the reference branches, two tube diameters can thus be measured with ideal optical coupling. The parallel radiation path can include an empty tube or no tube. The correction occurs respectively by way of the values obtained in the reference branch. These can also be included in the correction in a modified manner.

Based on a thusly configured sensor a radiation barrier between the radiation source and the radiation detector is advantageous as a measure for increasing accuracy. Only the shielding of the radiation source and, depending on the circumstances, the detectors at the surface to the measuring object enables the accurate definition of the light paths and with this the distances d. Because when using un-housed components a contact of the components with the measuring object may lead to damage to the connecting elements, for example due to tearing off of bond-wires or damage due to punctual mechanical force input, a measuring involving contact is only possible by means of a spacer or through a protective cover. Also aspects of the sensor application require the possibility of a cleaning a protective cover. Such a protective cover can be made of a protective window made of plastic or glass arranged at a short distance to the component or can also be made of a filling of protruding components or connecting elements with a cast mass that is transparent for the radiation. A conduction of radiation between the boundary surfaces of a transparent protective window or a reflectance at the surface of a cast mass that is transparent for the radiation cannot be prevented.

The radiation propagation from the component to the radiation input site situated on the measuring object is thus not possible direct and optical crosstalk is possible. Preferably the undesired, since non-signal carrying, irradiation from the radiation source to the detector or detectors without passage though the measuring object is prevented by a radiation barrier. This radiation barrier must have a sufficiently high damping, i.e., thickness>($3/\mu a$ of the radiation barrier material), and serves for reducing background light/external light/interfering light which additionally cause noise in the detector. In addition also a further radiation barrier around the radiation sources and detectors can be provided. Further radiation barriers are advantageous that limit the detected surface of the measuring object for each detector so that the distance between the location of the radiation input and the detection location can be determined more accurately and in particular radiation portions which are only scattered below the radiation source in the measuring object and hit a further distanced or closer detector at an angle are so to speak assigned "erroneously" to a distance d.

On the other hand the barrier reduces the influence of a variance caused by the sensor arrangement of the optical crosstalk by handling or different environments.

The separation of the protective cover has a similar effect. The further conduction by reflectance on one or both boundary surfaces of a flat protective cover is coupled out at the end of the protective cover and can no longer enter the detector. Thus the separation of the protective cover is preferably provided between the radiation input side and the detection side and according to another feature of the invention the separation of the protective cover is also provided for each of the detection distances.

The radiation barrier is preferably configured so that the direct irradiation via a protective cover as well as the radiation transmission in particular via the substrate that carries the components and the surrounding housing components is avoided. According to the state of the art this can result from the coatings that are strongly absorbent for the used wavelengths (lacquers, metal coatings etc) as well as from screens that strongly absorb the radiation or appropriately arranged cast masses that strongly absorb the radiation. A possible configuration for such cast masses involves the use of a transparent cast mass on the sensor, wherein slots or grooves are introduced into the transparent cast mass as far as to the substrate that carries the components, which slots are filled with non-transparent cast mass.

Another embodiment for such cast masses would be the filling of hollow spaces in the sensor housing which only leave open a direct region of the radiation propagation from the radiation source to the surface of the measuring object and of the object to be detected at the distance d on the surface of the measuring object to the detector or detectors. According to another feature of the invention such gaps may be generated in the absorbing cast mass by a prior placed geometrically predetermined transparent cast mass or other devices that are transparent for the radiation.

Also in the case of the substrate that carries the component the substrate parts that carry the radiation sources and the detectors can be mechanically separated.

A further advantageous solution is to have the radiation barrier slightly protrude out of the surface that has to be brought to the measuring object, for example in that the radiation barrier protrudes by between 0.1 mm and 1 mm over a provided contact surface with the measuring object. When this protruding radiation barrier can be pushed into the (soft) surface of the measuring object or when the barrier is deformable, the optical crosstalk that is caused by an air gap, i.e., the bleed-over of radiation from the radiation source into the detector or detectors without passing though the measuring object, can surprisingly effectively be prevented. When the measuring object is not sufficiently soft a greater air gap forms on one side (than without protruding barrier) which however is delimited by the radiation barrier. Also in this case an optical crosstalk is prevented.

A further design variable is the thermal influence of the component characteristics or the measuring object. Thus it is generally advantageous to use components that are as temperature independent as possible.

When the optical properties of the measuring object change with the temperature the temperature of the measuring object at the contact surface with the sensor has to be detected and taken into account for the analysis.

Also any change of the component properties caused by the temperature is problematic. It is known that in the case of LEDs as radiation sources electric current flowing through the LEDs increases the temperature and the radiation output is reduced. A temperature increase also has an influence on the detectors, thus in a silicone-photodiode for wavelengths<500 nm an increased sensitivity was observed with an increase of the temperature from room temperature to about 45° C., i.e., an increased signal at same radiation amount. At other wavelengths or in the case of other components or temperature ranges different changes are observed. It is also known that with increasing temperature the electronic amplification introduces noise into the signal. The influence of temperature on the components leads to different accuracies in the quantification when the respective temperatures of the components are not controlled or known and their influence or influences are corrected.

These heat influences can be corrected by detecting the temperature of the components or the temperature in the vicinity of the components in prior measurements. The corrections can also be accomplished by using data sheets/manufacturer specifications. The correction is performed after the detection of the sensor values during the analysis of the amplified signal or electronically as analog adjustment of the total amplification to a linear characteristic curve with components in the control feedback loop of the amplifier that change inversely with the temperature with regard to the temperature characteristic curve of the component to be corrected or parallel to the component to be corrected. Also advantageous is a controllable component, which adjusts the actual enhancement by way of the signal values, for example a digital potentiometer that is controlled by a processing device. Such a temperature detection is preferably performed on the substrate in the vicinity of the components.

Preferably also a thermal shielding of the radiation sources from the detectors and the appropriate material selection for the substrate carrying the component is provided, to ensure that the components are largely on the same temperature level due to high heat conduction. A heat conduction originating from the radiation sources as primary heat sources in the sensor is not vey advantageous because viewed over the sensor, i.e., on the detectors that are positioned at the different distance d, would always generate a temperature gradient.

Also preferred is the use of components for increasing the temperature to a stabilized level, which is either above the level reached during normal operation or at which the changes of the component properties during operation are sufficiently minor in order to ensure a sufficiently high accuracy of the signals which corresponds to the change of the amount of substrate to be resolved. The temperature is to be detected and to be stabilized to a target value by regulated heat input.

FIG. 4 shows an exemplary solution of stabilizing the temperature of a component-carrying substrate. The circuit heats the radiation sources via the resistor R6, which is thermally coupled with the resistor R7. The time constant for the regulation is set via the configuration of R1 and C1. The time constant set therewith should advantageously correspond to the time constant of the thermal coupling between R6 and R7 so that the regulatory circuit can regulate stably. C2 serves for suppressing the vibration tendency of the regulatory circuit. The resistors R3 divide the voltage to half of the voltage U2. When a voltage source for multiple electronic circuits is provided U2 can in this case be supplied by this voltage source. When no further voltage source is present U2 can also be identical to U1. From U1 flows the current for heating the resistor R6, whereby an separate current circuit is advantageous.

The bridge circuit is regulated with the temperature-stable branch, which is formed by the resistors R3 and R3 and the temperature-dependent branch, which is formed by the resistors R4 and R5 as well as R7 to voltage parity in the bridge. IC1 enhances the deviations occurring in the bridge circuit and controls the transistor T1, which impinges the heating resistor R6 with current until the resistor R7 prevents this via the change due to the thermal feed back via the IC1.

The system can maintain a target temperature predeterminable via the resistors R4 and R5 in a purely analog manner without digital control. R4 serves only for adjusting the values that can be set with R5 and is not required. When the voltage value, which is present at the Temp sens is analyzed the temperature that is present at R7 can be determined thereby.

Also preferred is a thermally well conducting connection of all components or only to radiation sources or only the detectors or the radiation sources and detectors as thermally separate groups and an efficient cooling to the level of the ambient temperature associated therewith. As an effect the components heat up for each measurement starting from the ambient temperature and thus exhibit at each measurement cycle a same characteristic. An offset that build up over the measurements due to the temperature influences is thus prevented. The heat dissipation has to be correspondingly be great in order to limit a temperature increases of the component to several Kelvins.

Similar considerations as for the detectors arranged at different distances d also apply to the reference detector that detects the radiation of the radiation source(s). The reverence detector can also be utilized for the stabilization measures and correction possibilities for the detectors.

The sensor design corresponding to the invention has thus been described. Following is the configuration of the measurement or measurement analysis advantageously performed with the sensor.

The process of measuring with the sensor provides that for each measurement a dark correction is performed with which the amount of radiation impacting the detector or detectors when the radiation source is not activated and the offset (dark value) caused by the signal detection device is determined.

Without departing from the inventive idea the interferences can also be detected by shining light through a parallel beam path (reference branch) in absence of the measuring object.

In the following step the determined interference and/or the dark value is subtracted from the radiation amount impacting the respective detector or detectors at activated radiation source, which radiation amount also contains the offset and/or the interference and with this the interference caused by external light and characteristics of the signal detection device are significantly reduced. The increased accuracy resulting therefrom leads enables quantifying smaller concentration changes of the target substance.

For increasing the accuracy the measuring process also provides for repeating measurements, in a temporal sequence that avoids physiological influences and/or influences caused by external light. The repetition of measuring processes under the same measuring conditions allows for averaging prior to or after the analysis thereby reducing the influence of noise and other interfering variables because their influence—when fully detected—has a positive and also negative impact on the measuring value at the detector. The repetition of measuring processes under the same measuring conditions also reduces the influence of interferences that vary over time. In particular factors that play a role in this case are the frequency of the ambient light sources (50 Hz or 60 Hz, depending on the mains supply voltage frequency or in the light output 100 Hz or 120 Hz) blood pulsations caused by the heart beat or general blood pulsations occurring during measurements on the skin that are caused by metabolism-dependent regulatory mechanisms, or in the case of measurements at other measuring objects, but also motion artifacts or breathing movements or during measurements on other measuring objects the frequencies of these objects of the repeating processes and multiples thereof. Hereby different strategies for different types of interferences are provided:

When the interference is sinusoid with a constant frequency it is advantageous to the average two measurements taken at a temporal distance of 1(2*interfering frequency).

Further preferred is the measurement over one or multiple complete periods of the interference because the influences can then be averaged to a constant value which can be corrected by the comparison during analysis of the measuring signals with a reference method for determining the concentration of the desired target substance (process see below in the description of the analysis) detected and corrected.

When averaging over very long time periods compared to the interference time period a further strategy is that the used measurement duration and its repetition frequency advantageously does not correspond to the interfering frequencies or multiples thereof.

The number of repetitions should be as high as possible, and is limited by the intended measuring duration until the target value is determined, and by undesired changes in the measuring object that influence the mean value of the detected radiation amount, for example in the case of skin caused by thermal regulation processes with time constants in the minutes range.

Advantageously also the lock-in-technique can be used to suppress interferences by using frequencies that are different from the interfering sequences, and for achieving a high accuracy also different from multiples of the interfering sequences.

A further advantageous solution for reducing optically active interferences is the detection of the interfering variables as interfering sensor signals in the immediate vicinity of the sensor or at the sensor in order to then correct these interferences in a targeted manner. The correction can be performed by a coupling of the detected and intensity-corrected interfering signals with the measurement values of the sensor in a degenerative feedback loop or also according to the invention by processing the interfering signals with a processing device.

After application on the measuring object the measurements are preferably analyzed with an own regulation system preferably after a short break, i.e., after the adaption period of the system. An example is the skin because initially the sensor displaces the blood when being placed on the skin, and after a short period of time blood flow is stabilized corresponding to the acting influence. During this adaption different average values of the detected radiation amount result and are advantageously not taken into account in the above-described averaging over a longer period of time.

The prediction (see below) of the quantity of one or multiple target substances or analysis of the measuring signals, i.e., the analysis of the radiation amounts detected by the detectors at different distances d, is accomplished according to the state-of-the-art by a predictive function for the amount of target substance present in the respective target volume with the radiation portions measured for each wavelength and each distance d (dark value corrected). The predictive function is developed by a regression analysis (chemometry). The measurements used for generating or calibrating the predictive function are taken with the sensor at a set of biological tissues or substance mixtures, wherein the entire variation breadth of the mixture composition is covered with the concentrations of all different components. The concentration of the target substance is determined in each case by a reference method.

As an alternative the substance mixture to be measured can be replaced by optical standards (Phantom), wherein the term optical standard (phantom) means substance mixture that is artificially mixed together from materials, which makes it possible to mimic the variety of the actual substance mixture and the geometric dimensions. The optical standard (phantom) can also be an active device, which detects the intensity of the radiation sources and conducts the required light amount to the detectors installed in the sensor in correspondence to the expected radiation amount at the detector positions. By adding of the substance to be determined or based on the use of reference methods concentration of the substances is known and can be used for the regression method.

It is also conceivable to determine the connection between sensor signals and the concentration of the substance to be determined by stimulated calculations. This requires the exact knowledge of the characteristics of the sensors and exact description of the light propagation in the substance mixture. For this purpose for example Monte Carlo simulations of the light propagation can be used for the numerical solution of the radiative transport equation.

The predictive function also includes the data preprocessing, which in an embodiment of the invention consists in transforming the backscatter signals measured at the detector into absorption data by calculation. Such a transformation can for example be accomplished by logarithmic or other mathematical operations. From the measurement values that have been approximately transformed into the absorption data by the logarithmic operation data the sought after substance concentration can be determined with less effort by regression analysis (chemometry). The regression analysis (chemometry) serves for determining the predictive function. The transformed values are calculated into the substance concentration by applying the predictive function.

Further pre-processing steps are for example the normalization of the detector measuring values for each wavelength to a uniform total sum, which for the detected spatially resolved backscatter signals provides independence of the radiation source intensity or other strategies known to the person skilled in the art.

The effort for determining the predictive function is significant and in the above mentioned form can only be used for a small number of sensors. As a result of the manufacturing process all sensors have a variance, for example regarding the properties of the components or the arrangement, which leads to a different relationship between the concentration or the target substance and the sensor signals, i.e., the transmission function (i.e., signal transfer function) of each sensor has to be adjusted for the correct function of the sensor when the variance is of a magnitude that the desired accuracy cannot be achieved.

Because hereby the high sensitivity of the sensor for small amounts or small changes of the target substance is a significant criterion, all influences on the radiation amount at the detectors have to be controlled, which is ensured by the above-described technical measures regarding the sensor design and the measuring process. Regarding a serial production the goal is to avoid conducting laborious measurements for each individual sensor that is subject to tolerances using series of different concentrations of a multitude of substance mixtures (measuring object), but rather the calibration is transferred to the individual sensor using measurements conducted on a few optical standards (phantom).

Advantageously comparative measurements of calibrated sensors and non-calibrated sensors on one or multiple optical standards (phantom) makes it possible to deduce a computing instruction for the calibration transfer, with which a transfer function (signal transfer function) from the calibrated sensors to the non-calibrated sensors can be transferred or adjusted for the non-calibrated sensors. This computing instruction determines the necessary changes in the transfer function (signal transfer function). The measured detector measurement values are transferred by the transfer function (signal transfer function) as input variables for the prediction function of the target substance. This transformation occurs in a manner so that the transfer values are transformed into a target value in a common value range that is the same for all sensor signals.

It is also advantageous to provide the calibration transfer data determined for the individually calibrated sensor together with the measurement values and to take these into account in the subsequent applied predictive function, i.e., when transforming the sensor data into the concentration of the target substance.

According to another feature of the invention the sensor is constructed so that a computing device is integrated as programmable data processing, which via the channel that provides the measurement results after applying the transfer function (signal transfer function) by the programmed pre-processing, enables a new input of a changed programmed pre-processing.

This approach for transferring the calibration however is only successful when certain preconditions are satisfied. The optical standard or standards (phantom) which are used for the comparative measurement, have to be similar to the real measuring object regarding their optical properties and geometric dimensions, so that a similar radiation distribution for measuring the transfer properties can be used. When the optical properties of the measuring object vary over a broad range multiple optical standards (phantom) that cover the range of variation have to be used and the computing instruction for the calibration transfer (calibration transfer function) has to be determined. In the case of small tolerances regarding the components and component arrangement and a construction that corresponds to the above-described measures, it is possible to realize a linear calibration transfer function, so that a phantom for calibration transfer is sufficient. When the calibration transfer function is nonlinear, the transfer can be performed with multiple optical standards (phantom).

In addition for the calibration transfer strong dependencies of the transfer function (signal transfer function) of the sensors or predictive function of tolerances for optical properties of the measuring object or environmental conditions should be avoided by constructive measures and by way of the analysis process. Thus the constructive design of the sensor and the analysis are directly linked with the mass production of uniformly accurately measuring sensor units.

As a result of the combination of the described analysis methods with a selection of same components and the measures for sensor design it can be achieved that the variances of the sensor units, i.e., the individual transfer functions (signal transfer function), lower the accuracy to a very minor degree, when a calibration is used and this calibration transfer is linear.

An essential criterion for the used optical standards (phantom) for calibration transfer is a uniform light distribution, and similar geometric dimensions as in the measuring object. This not only applies to same optical parameters but also to aspects of light distribution due to mechanical properties, surface properties, etc. A uniform light distribution is achieved by using an optical standards (phantom) that have optical parameters in the range of the variance occurring at the measuring object phantom and ensuring that the condition at the surface of the optical standard (phantom) are similar to those of the measuring object so that no different effect on the light distribution occurs.

This can also be seen by the fact that the effect of the radiation barrier on the radiation distribution in the measuring object and the optical standard or standards (phantom) for the calibration transfer is the same.

The calibration transfer for a serial production thus occurs in two steps. At one or multiple artificial calibration transfer means, for example an optical standard (phantom) having optical parameters that result in a radiation distribution similar to that of the real measuring object, a reference measurement is performed with an already calibrated sensor. In the second step the calibration is transferred by comparing the signals (comparison) of this reference measurement with the signals obtained from a corresponding measurement performed with a non-calibrated sensor at the same optical standards (phantom) and changing the parameters of the predictive function with the calibration transfer function.

In the following invention is described and embodiments of the invention.

The goal of the invention is achieved by a spatially resolving optical sensor device with multiple radiation sources or with one source with multiple wavelength ranges and multiple radiation detectors or with one radiation detector with multiple separately readable subunits for the spatially resolved detection of target substances in strongly scattering measuring objects and a radiation barrier which is configured to absorb and/or to reflect radiation of at least one wavelength range. The radiation sources are arranged at a defined distance to the radiation detectors and are arranged so as to be separated by the radiation barrier from the radiation detectors so that the radiation generated by the radiation sources, before impacting the radiation detectors, first traverse a path length through the measuring object.

In an embodiment the radiation barrier protrudes over a provided contact surface with a measuring object by between 0.1 mm and 1 mm.

In an embodiment the radiation barrier includes a component-carrying substrate and/or a housing that surrounds the radiation sources and thereby blocks the propagation of radiation in the substrate and/or through the housing.

In an embodiment further radiation barriers enclose each detector with a delimited closing opening at the contact surface to the measuring object.

In an embodiment the radiation penetrates the measuring object up to a predetermined depth when traveling from one of the sources to one of the detectors positioned at a defined distance.

In an embodiment at least two radiation detectors are arranged at different distances to the radiation sources.

In an embodiment the device has at least two radiation sources with at least two different wavelength ranges that are selected so that at least one respective wavelength or one wavelength range is used in which for each target substance to be determined the sensor signals have clear effects on the radiation amounts detected by the radiation detector or detectors. For determining interfering substances or other interfering influences at least one wavelength or wavelength range can be used in which one or multiple target substances have a very minor or no effect on the sensor signals, i.e., the interfering substances however show greater effects on the sensor signals for the radiation amounts detected by the radiation detector or detectors.

In an embodiment of the device at least one radiation source with more than two wavelengths or wavelength ranges can be used so that for each interfering variable at least one wavelength or one wavelength range is radiated in and by using more than one source in the wavelength range of the target substance the sensitivity for this substance is increased or subclasses of the target substance can be resolved.

In an embodiment of the device the signals obtained from detectors arranged at different distances are amplified so that the signal amplitudes for all detectors are similar, or the surface or the number of the detectors for a defined distance is respectively selected so that the signal aptitudes are similar for all distances.

In an embodiment of the device a first type of signals can be detected with the detectors after switching on a radiation source and a second type of signals can be detected with the detectors after turning the radiation source off and by subtracting the two types of signals from each other a further result signal is obtained for further analysis, or the signals can be detected at a respective different intensity of the radiation source and can be subtracted from each other in thereby a further results signal can be obtained for further analysis.

In an embodiment a defined portion of the radiation of the sources can be conducted to a reference detector and with the reference detector a signal can be detected while the radiation source is turned on and subsequently another signal can be detected while the radiation source is turned off, the two signals can be subtracted to obtain a reference signal and the respective result signals for each source are separately divided by the thusly obtained reference signal to obtain an intensity-independent signal for further analysis.

In an embodiment un-housed light emitting diodes are used as radiation sources which can be placed very close to each other so that the measuring object can be substantially uniformly irradiated by all light emitting diodes.

In an embodiment the sensor device includes a temperature-setting device. The temperature-setting device can set the temperature of the sensor device, in particular the temperature-setting device is configured to heat and/or cool radiation sources, for example light emitting diodes, or detectors or both, so that the temperature of the radiation sources can be set to a predetermined temperature value.

In an embodiment a broadband light source is used as radiation source. In this case a spectrometer is used as radiation detector for the radiation detection or a component with exchangeable filters is provided.

In an embodiment the radiation of the radiation sources is conducted onto the measuring object by means of one or multiple optical elements such as for example light conductors, lens, prism, glass rod, mirror, beam splitter, window, cast mass or other optical elements. The radiation exiting from the measuring object can be conducted onto the radiation detectors by means of one or multiple other optical elements or the same optical elements.

In an embodiment the radiation sources, the radiation detectors and all optical elements are configured with such a small tolerance, so that the calibration can be transferred with sufficient accuracy.

The accuracy demands placed on the signals hereby results from an error propagation to the error of the predictive value of the target variable. The mathematical relationship is generated via the partial derivation of the predictive function with regard to the signal:

Error of the target value =
$$\sqrt{\Sigma_{all\_signals\_n}\left(\frac{\partial\_predictive\_function}{\partial\_signal\_n} - error\_signal\_n\right)^2}$$

In an embodiment all signals are measured in the same manner repeatedly and all signals obtained in the same manner are outputted.

(Analysis, Calibration, Mass Production)

In an embodiment a serial measurement is conducted with a sensor device on measuring objects or substance mixtures that have properties that are similar to the measuring object regarding the target substance and regarding interfering variables, in which serial measurement the concentration of the target substance as reference value is varied in a targeted manner or is known as a result of a different method at different measuring objects and in which interferences are varied and a calibration rule is determined which enables a prediction of the concentration of the target substance and with this is available to the sensor device as reference sensor device with a reference calibration for a subsequent calibration transfer.

In an embodiment signal preprocessing steps are performed beforehand for the reference calibration, which involve determining the logarithm of the result signals or the normed signals and the reference values are calculated with a fractional power into the input variables for the predictive function.

In an embodiment the reference calibration is transferred with a calibration transfer signal to further constructively similar sensor devices, by performing comparative measurements with reference sensor devices and the constructively similar sensor devices and the signal transfer function of the constructively similar sensor device is adjusted in the event of excessive deviation.

In an embodiment the calibration transfer means are one or multiple artificial measuring objects, for example substance mixtures which have similar optical properties regarding absorption and scattering and whose properties can be tested with a separate method so that a change in the course of aging can be tested.

In an embodiment a calibration transfer function can be deduced from the measurements conducted with the reference sensor device and the constructively similar sensor devices in the calibration transfer means, which calibration transfer function reduces by calculation the remaining differences between the reference sensor device and constructively similar sensor of devices to the degree that the signal levels of the constructively similar sensor devices after calculation with the transfer function corresponding to the calibration transfer function correspond to those of the reference sensor device and subsequently the predictive function of the reference sensor device can be applied with no or very little loss of accuracy for the prediction of the concentration of the target substance in the constructively similar sensor devices.

In an embodiment the same preprocessing steps can be applied to the signals of the constructively similar sensor devices as to the reference sensor device. In this case the signals are combined in a mathematically ordered structure, so that they are calculated with the transfer function (signal transfer function) element by element and with this corresponding signal level can be transferred in the reference sensor and can subsequently be calculated element by element with the (for all sensor devices similar) predictive function to form a prediction regarding the concentration of the target substance.

Specific Embodiments

In an embodiment the target substance or target substances to be measured in the skin are antioxidants, i.e., flavonoids or carotinoids, in particular beta-carotin, lycopin, lutein, zeaxanthin or capsanthin that are measured in the epidermis and dermis.

In an embodiment radiation sources are used that are in the wavelength range of 380 to 800 nm and are realized by narrow-band radiation sources, for example light sources with medium wavelengths of 405 nm, 430 nm one 435 nm, 470 nm, 500 nm, 525 nm and 700 nm. As radiation detectors for example silicone-photodiodes with an edge length of 1 mm and mean distances to the light sources of 1 to 7 mm or also similar construction geometries can be used.

In an embodiment the radiation sources and radiation detectors are closed towards the skin by a respective window. Between the radiation sources and the radiation detectors a radiation barrier can be located which ends flush with or protrudes over the windows towards the skin.

In an embodiment the radiation sources and radiation detectors are each enclosed by a cast mass. Also in this case a radiation barrier can be located between them, which can be formed by sawing in a recess and casting in an absorbing mass or by way of a pre-mounted component with sufficient radiation-damping properties. Preferably the radiation barrier respectively ends flush towards the skin or protrudes over the skin.

In an embodiment different distances between the radiation source and the radiation detector can be analyzed separately and thus for example a carotinoid content (antioxidant value) can be determined for the epidermis at small distances in the range of 0.5 mm to 4 mm and for the dermis at greater distances of 2 mm to 8 mm.

In an embodiment the antioxidants can be analyzed separately for different subclasses, by selecting respective radiation source for each subclass so that it's mean wavelength corresponds to the wavelength of an absorption maximum of the subclass of the antioxidants.

In an embodiment the prediction of the antioxidant value is calculated in the sensor device and is transmitted via a communication interface to an output device, display device or mobile device.

In an embodiment the substance to be measured is water that can be measured in different concentrations in the epidermis, dermis and the subcutis and is evaluated time-dependent as water incorporation in case of a heart insufficiency or also for the evaluation of a sufficient liquid intake or kidney function.

In an embodiment radiation sources in the wavelength range of 900 to 2100 nm are used and realized by small-band radiation sources, for example light sources with mean wavelengths of 975 nm, 1160 nm, 1220 nm, 1320 nm, 1470 nm, and 1070 nm.

As radiation detectors indium-gallium arsenate-photodiodes with an edge length of 1 mm and mean distances to the light sources from 2 to 12 mm, or similar arrangement geometries can be used in order to determine or predict a water content.

In an embodiment the radiation sources and radiation detectors are each closed by a window that can be configured transparent or as a band-pass for a wavelength range of the radiation source. There between a radiation barrier can be arranged which can be flush towards the skin or can protrude over it.

In an embodiment the radiation sources and radiation detectors are each closed by a cast mass. In this case the radiation barrier is preferably arranged between the radiation sources and the radiation detectors, which is accomplished by sawing and casting with an absorbing mass or by a pre-mounted component with sufficient radiation-damping properties, wherein the radiation barrier in each case ends flush towards the skin or protrudes over it or the sources can be transmitted towards the exit window by a prism or similar radiation transmitting element.

In an embodiment the radiation sources are arranged separate from the detectors and are separated by a radiation barrier, wherein the radiation barrier in each case ends flush towards the skin or protrudes over it and the sources can be transmitted towards the exit window via a prism warms similar radiation transmitting element.

In an embodiment different distances between radiation sources and radiation detectors can be analyzed, so that a water content for the dermis can be determined at small distances in the range of 1 mm to 6 mm and for the subcutis at greater distances of 3 mm to 15 mm.

In an embodiment the water content can be separately analyzed by way of wavelength-dependent differences of the penetration depth for the dermis and the subcutis, by using radiation sources with smaller water absorption and with this higher penetration depth for the subcutis and by using radiation sources with higher water absorption and with his lower penetration depth for the dermis.

In an embodiment the influence of the water content in the epidermis can be eliminated as interfering variable from the calculations of the water content in the dermis and the subcutis by using the different depth weighting at the different distances of the radiation detectors to the radiation sources for the analysis.

In an embodiment the target substance to be measured is hemoglobin and oxygenated hemoglobin and hematocrit in the blood in an extra corporal blood circulation during dialysis or the apheresis of blood or a different situation in which a portion of the blood is situated in a tube system or a cuvette as measuring site.

In an embodiment radiation sources in the wavelength range of 380 to 900 nm are used and are realized by small-band radiation sources, for example light sources with mean wavelengths±tolerance range of 730 nm±30 nm, 807.5 nm±2.5 nm and 850 nm±20 nm. As radiation sources for example silicone-photodiodes with an edge length of 1 to 3 mm and average distances to the radiation sources of 2 to 12 mm or also similar arrangement geometries are used depending on the dimension of the tube system or the cuvette.

In an embodiment the radiation sources and radiation detectors can each be closed by a window and a radiation barrier can be arranged between the radiation sources and the radiation detectors, which radiation barrier ends flush toward the windows or the tube or protrudes over it.

In an embodiment the radiation detectors are all of the same type and are arranged on a material with good heat conductivity so as to have a uniform characteristic and same temperature.

In an embodiment the target substances to be measured are fat, water and protein in animal tissue or meat products which are either present as-grown or partially homogenized in a processing step.

In an embodiment the sensor device has radiation sources in the wavelength range of 900 to 2500 nm which are realized by small-band radiation sources, for example light sources with average wavelengths of 910 nm, 1200 nm, 1450 nm, 1550 nm, 1680 nm and 1720 nm. As radiation detectors for example indium-gallium arsenide photodiodes can be used with an edge length of 1 to 3 mm and average distances to the radiation sources of 2 to 12 mm or also similar arrangement geometries in order to determine or predict a separate fat, water and protein content.

In an embodiment the variables to be measured are a light damping in the epidermis and a sun-protection factor in the skin provided by a sunscreen product.

In an embodiment radiation sources in the wavelength range of UV light, visible light, or near-infrared light are used and can be between 280 nm and 1100 nm and can for example be realized by broadband light sources such as xenon-light sources. For the radiation detection a radiation detector constructed as a spectrometer, for example with silicone radiation detectors, can be used.

In an embodiment radiation sources in the wavelength range of UV light, visible and near-infrared light are used and can be between 280 nm and 1100 nm and can be realized for example by at least one small-band light source, such as light emitting diodes. For radiation detection a silicone radiation detector is used.

In an embodiment the radiation of the radiation sources can be transmitted by one or multiple optical fiber toward the skin. The radiation which optionally exits from the skin t different distances to the optical fibers can be transmitted by one or multiple optical fibers though the spectrometer for radiation detection. The optical fibers can have a diameter of 50 to 600 µm. The optical fibers can form a radiation barrier based on their optical properties themselves or this barrier function of the optical fibers can be enhanced by introducing embedding means or absorbing sleeves.

In an embodiment the different optical fibers of radiation sources and radiation detectors are assigned a respective distance. In this case a light damping caused by the skin can be determined therefrom and a part of the distances can enable a determination of the damping caused, solely by the epidermis or parts of the epidermis.

In an embodiment a wavelength-dependent determination of the damping of the radiation though the epidermis or parts of the epidermis prior to or after the application of sunscreen allows determining the sun protection factor or a wavelength-dependent sun protection factor.

In an embodiment the target substance to be measured is melanin, which is measured in the skin in the epidermis.

In an embodiment the radiation sources emit in the wavelength range 300 to 800 nm and are realized by small-band radiation sources such as light sources with mean wavelengths of 430 nm, 450 nm, 470 nm, 500 nm, 630 nm, 700 nm. As radiation detectors for example silicone-photodiodes with an edge length of 1 mm and average distances to the radiation sources of 1 to 5 mm, or similar arrangement geometries can be used.

In an embodiment the radiation sources and radiation detectors are each closed by a window. Between the radiation sources and radiation detectors a radiation barrier can be arranged, which can end flush with or protrude over the windows towards the skin.

In an embodiment different distances of the radiation sources and radiation detectors are used in order to cancel the influence of the dermis and subcutis out of the calculation of the melamine value of the epidermis.

In an embodiment the radiation sources and radiation detectors are each closed by a cast mass. There between a radiation barrier can be arranged, which can be implemented by sawing and casting with an absorbing mass or by a pre-mounted component with sufficient radiation-damping properties, wherein the radiation barrier in each case ends flush towards the skin or can protrude over it.

In an embodiment a value for the skin type can be deduced from the melanin content.

In an embodiment the target substance to be measured is bilirubin, which is measured in the dermis in the skin.

In an embodiment the used radiation sources have a wavelength range of 300 to 800 nm and are realized by small-band radiation sources, for example light sources with average wavelengths of 430 nm 450 nm, 470 nm, 500 nm, 630 nm, 700 nm. As radiation detectors for example silicone photodiodes with an edge length of 1 mm and average distances to the light source from 1 to 5 mm, or also similar arrangement geometries can be used.

In an embodiment of the radiation sources and radiation detectors are each closed by a window. There between a radiation barrier can be arranged, which can end flush with or protrude over the window towards the skin.

In an embodiment the different distances of radiation sources and radiation detectors can be used to cancel the influence of the epidermis and the subcutis out of the calculation of the bilirubin content for the dermis.

In an embodiment the radiation sources and radiation detectors are each closed by a cast mass. There between a radiation barrier can be arranged, which can be implemented by sawing and casting with an absorbing mass or by a pre-mounted component with sufficient radiation-damping properties, wherein the radiation barrier in each case can end flush with or protrude over it toward the skin.

DETAILED DESCRIPTION OF PREFERRED EMBODIMENTS

The exemplary embodiments shown in the following drawings are concrete embodiments of the general technical solutions described in the text above.

Antioxidant Sensor

Figure 5:
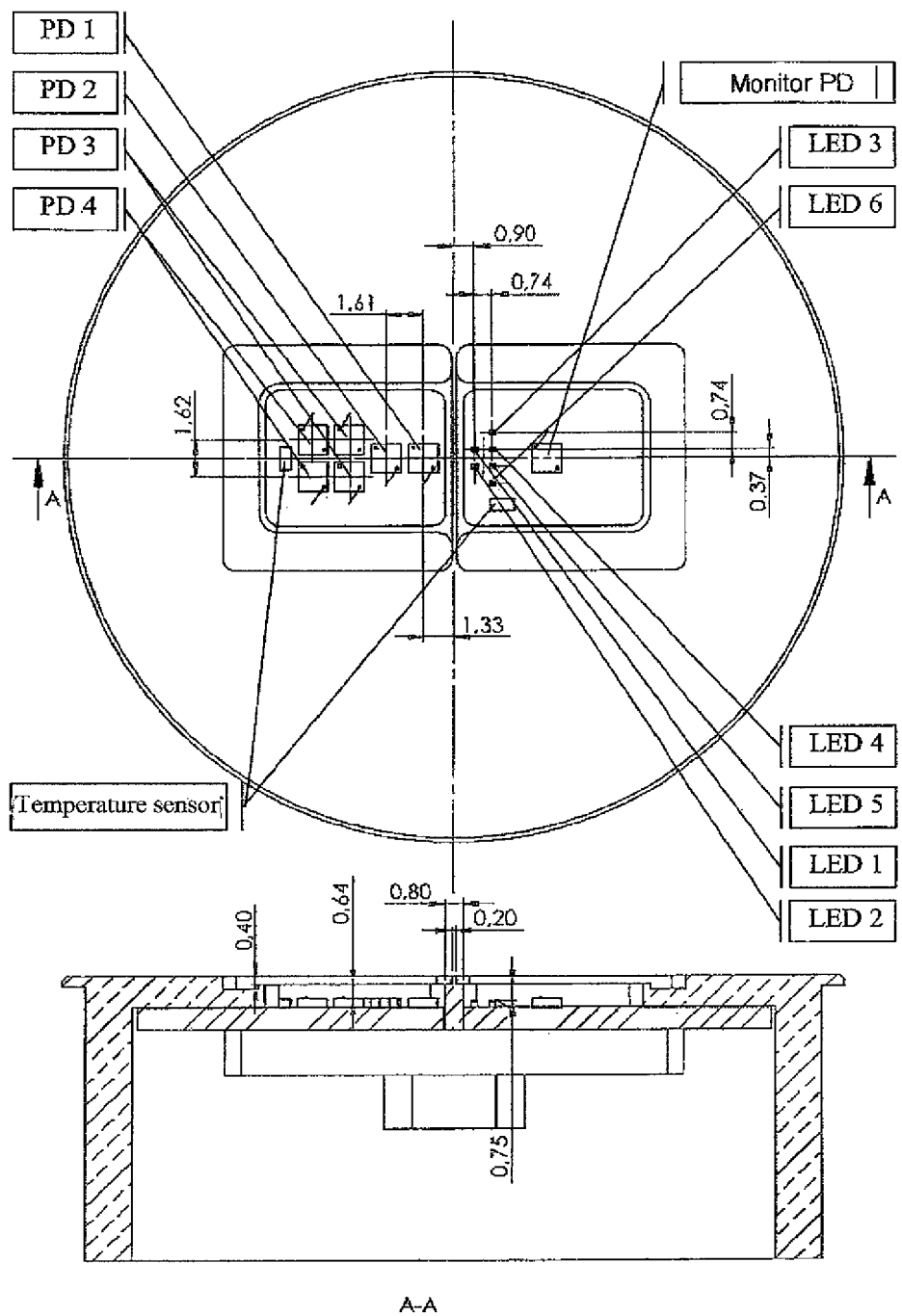

An exemplary embodiment for the sensor for detecting substances with anti-oxidant activity in the skin, in particular beta-carotin and lycopin, is shown in FIG. 5. The main interfering variables during the detection are hemoglobin and melanin. The sensor includes six radiation sources each constructed as a chip-LED with 300 μm side length, with the average wavelengths 405 nm, 435 nm, 470 nm, 500 nm, 525 nm, 700 nm and six chip-photodiodes made of silicone as detectors with 1.000 mm side length with the center distances LED1 to PD1=2.23 mm, LED1 to PD2=3.84 nm, LED1 to PD3=5.45 mm, LED1 to PD4=7.06 mm and a monitoring-photodiode (monitoring PD) which is arranged at the distance of 2.6 mm to the LED1 but in opposite direction to the other photodiodes and is identical to the above-mentioned photodiodes. The photodiodes designated PD3 and PD4 are arranged adjacent each other at the distance 1.62 mm to each other and are electrically connected parallel upstream to the amplifier. LED2 is arranged on the sensor board (or also sensor board) in an axis that is perpendicular to the axis LED1-PD4 at a distance 0.74 mm to LED1. LED3 to LED6 are arranged on an axis that is parallel to the axis LED1-LED2 which is spaced apart 0.74 mm further from the PDs. Between the LED3 to LED6 a distance of 0.74 mm is present.

The wavelengths of the LED can deviate by several manometers without adversely affecting the function of the sensor.

The LEDs are mounted on a light source board and the photodiodes on a detector board together with a respective temperature sensor on the same surface so that all components are arranged on the same side. Both boards are mounted together on a carrier of a black anodized aluminum alloy, which each has a recess of respectively 6×7.8 mm² for the light transmittance above the light source board and the detector board, which are closed liquid-tight with a transparent window made of glass. Between the windows and the two boards a radiation barrier is formed in the carrier.

The size of the recess can advantageously be reduced or be configured differently corresponding to the principles discussed above or according to the state of the art without changing its accuracy insofar the signal of the detectors is not obscured by the noise.

Both boards together form the sensor board, which is connected with a signal detection board with a separate amplification for each sensor and analog-to-digital conversion of the signals as well as a further board with a microprocessor for controlling the signal detection. This microprocessor board also includes a communication interface, which can be configured as a wireless and cable-based interface according to the state of the art. The communication and control of the energy supply can also be performed on a separate board and can be electrically connected with the remaining boards.

A different construction of the functional unit is conceivable without departing from the invention. In particular the analog-to-digital conversion can be placed together with the detectors on one board and also the radiation sources and detectors can be placed on one board.

In the microcontroller a firmware-routine detects the digital signals and logarithmizes the signals. Other data pre-processing steps as described above are also advantageous. By means of a calibration function a prediction for the concentration of the antioxidants in the skin is subsequently outputted via the communication interface. The calibration function consists of two parts, the transfer function (signal transfer function) and the predictive function. The first part, the transfer function (signal transfer function), is valid for the respective sensor and is adjusted by a calibration transfer function, which contains the individual tolerances for the individual sensors and is derived from a comparative measurement of standards with a calibrated (reference)sensor and the individual sensor. The uncorrected transfer function (signal transfer function) for the sensor type and the calibration transfer function are present as matrix (LEDi×PDj), which are transformed by element by element multiplication to a corrected transfer function (signal transfer function) with a standard signal range.

The second part of the calibration function, the predictive function, determines the prediction of the concentration of the target substance. This second part includes the pre-processing (log) of the values obtained from the transfer function (signal transfer function) and their multiplication with the coefficient from the regression analysis (chemometry) which are added up and an offset is added and are calculated to the substance concentration via mathematical operations such as for example square root formation and quadrating. Advantageously this calculation of the predictive function uses four different sets of coefficients, wherein the weighted average value of the thusly-determined concentrations of the target substance is the output of the sensor.

The measuring site of the sensor during operation is generally the skin, wherein areas without hair and with small curvature are preferred. Particularly suited measuring sites are the two palms of the hands below the thumbs or the little fingers because there the epidermis is sufficiently thick to obtain a separation of the epidermis and the deeper layers with only small amounts of antioxidants.

An alternative embodiment includes a changed geometrical arrangement of the LED and PD on a common board, so that slots thermally decouple the LED and photodiodes respectively form each other and from the remaining board.

Further, the radiation sources and detectors can be constructed as integrated component (module) with the same optical geometry and can be placed on the sensor board. Thus the module replaces the light source board and the detector board. After contacting by bonding the module is mechanically protected with a transparent cast mass made of epoxy resin (for example Hysol OS 4000 of the company Henkel). Between the light sources and the detectors a radiation barrier is retroactively introduced by sawing into the cast mass down to the board and subsequent casting of the sawing gap with strongly absorbing cast mass. In the same manner barriers between the photodiodes are introduced, wherein however awing is not performed down to the board. The module may also only include the radiation source or only the detectors with the predetermined distance and is used in the same manner as in the above-mentioned exemplary embodiment instead of the light source or the detector and is assembled as above to a complete sensor.

In the same manner and embodiment of the sensor module is constructed, wherein all above-described boards are also integrated in the cast block.

Water Content Sensor

Figure 6:
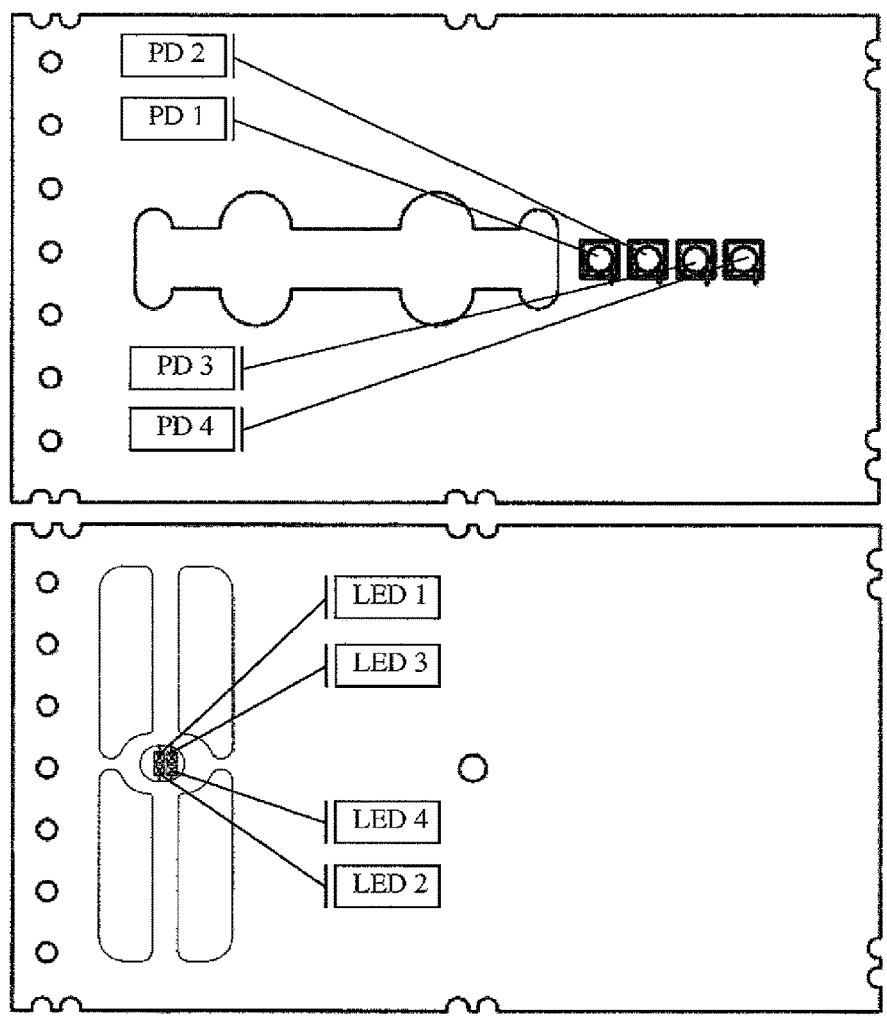

FIG. 6 shows an exemplary embodiment for a sensor for detecting the water content (or concentration of water) in the skin, in particular in the dermis and subcutis. The main interfering variable is the epidermis which is covered with sweat and has a different water content, the melanin content of the skin and different light scattering depending on the state of the skin. The sensor includes four radiation sources each constructed as a chip-LED with 300 mm side length, with the average wavelengths±tolerance range 975±5 nm, 1070±15 nm, 1160±15 nm, 1320±20 nm, and four Chip-photodiodes made of indium-gallium arsenide (InGaAs) as detectors with 1.000 mm side length.

It is also conceivable to exchange the LED-wavelength 1160 nm with a wavelength between 1150 to 1220 nm.

All LED radiate into a deflection prism with the dimensions 14 mm×2.5×2.5 mm$^2$, which functions as a light blender and causes a homogenous and uniform distribution of the light of each LED. The light is radiated from the deflection prism through a window with the dimensions 1.5 to 4 mm, which is placed on the skin. The deflection prism is advantageously covered with an absorbing cover except for the input and exit surface, which cover functions as radiation barrier prevents a crosstalk to the radiation detectors. The radiation detectors are arranged on an axis on the same board at a center distance of 2 mm to each other and a distance of 3 mm of the center of the PD to the center of the exit window. The PD are closed toward the skin with a housing into which a window with diameter 1 to 3 mm is introduced above each PD liquid-tight, which window has a high transmission in the spectral range of the LED and a small transmission in the visible spectral range and thus functions as daylight filter.

The here stated dimensions for the exit windows and the deflection prism can be varied without departing from the invention.

The LED are kept at a high temperature level, which is close to the achievable operating temperature determined in continuous operation. The temperature level is monitored by a temperature sensor. Other solutions according to the description above can also advantageously be used.

The radiation sources are arranged on an LED board, which is electrically connected with the sensor board and has the same dimensions as the sensor board. Advantageously the LED board is mechanically connected with the sensor board by a spacer.

The sensor board has the dimensions 15×40 mm$^2$ and carries the function of the signal detection with separate amplification for each sensor and analog-to-digital conversion of the signals and a microprocessor for controlling the signal detection. Via an electrical connection a communication and energy supply board is connected, which includes a communication interface, which can be configured as a wireless and cable based interface according to the state of the art.

A different construction of the functional units and other dimensions are conceivable without departing from the invention.

In the microcontroller a firmware-routine detects the digital signals and logarithmizes the signals. Other data preprocessing steps as described above are also advantageous. By means of a calibration function a prediction for the water content in the skin is subsequently outputted via the communication interface. The calibration function consists of two parts, the transfer function (signal transfer function) and the predictive function. The first part, the transfer function (signal transfer function), applies to the respective sensor and is adjusted by a calibration transfer function, which contains the tolerances for the individual sensor and is deduced from a comparative measurement on standards with a calibrated (reference)sensor and the individual sensor. The uncorrected transfer function (signal transfer function) for the sensor type and the calibration transfer function are each present as a matrix (LEDi×PDj) which transforms the measurement value matrix to a standard signal range by element by element multiplication to a corrected transfer function (Signal transfer function).

The second part of the calibration function, the predictive function, is a computation rule for determining the concentration of the target substance. This second part includes the pre-processing (log) of the values obtained from the transfer function (signal transfer function) and their multiplication with the coefficient from the regression analysis (chemometry), which are added up and are added with an offset and are calculated to the substance concentration via mathematical operations such as for example square root formation and quadrating.

The measuring site of the sensor during operation is generally the skin, wherein for monitoring chronic heart insufficiency in particular measuring sites on the leg, for example in the area of the ankle, are useful. For a general monitoring of the water metabolism or water content also measuring sites on the arm and the hand can be used.

Hematocrit/Oxygen Saturation

Figure 7:
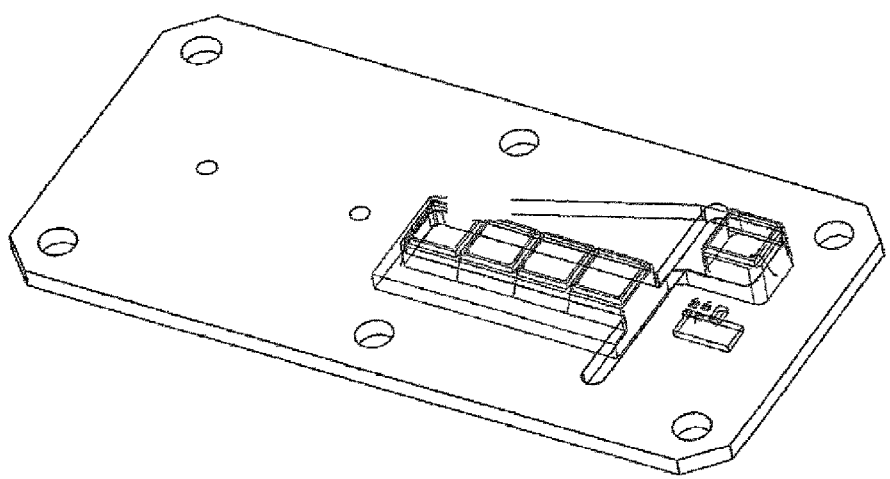
Figure 8:
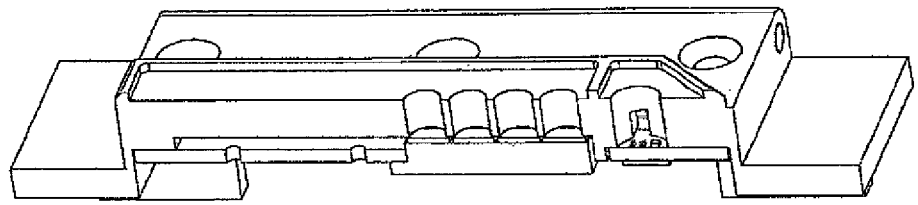

An exemplary embodiment for a sensor for detecting the hematocrit and the oxygen saturation of blood, for example during surgeries with heart-lung machines, is shown in FIG. 7 and FIG. 8. The measuring site is a cuvette or a tube through which blood flows, which in FIG. 8 are placed above the round openings and represent potential interfering variables due to having inherent tolerances or are being configured differently. In addition pump impulses interfere with the measurement of the optical properties of the blood and the blood components such as bilirubin and lipids. But also the blood cells themselves have a high individual variability regarding size and hemoglobin content, which interfere with a measurement.

The sensor includes four radiation sources each constructed as a chip-LED with 300 μm side length, with the wavelengths±tolerance range 730±30 nm (two identical LED installed diagonal relative to each other), 807.5±2.5 nm, 850±20 nm and four chip-photodiodes made of silicone as detectors with 2.6000 μm side length on a common sensor board into which a heat conducting carrier is integrated, which interconnects the photodiodes by a thermally highly conductive material, for example copper or another thermally highly conductive material, and is held on a temperature level above room temperature or a maximal temperature of the measuring object (for example 38 C). On the heat conducting carrier in the sensor board a monitoring photodiode is located, which is arranged at a distance of 5 mm to the LED1 at a right angle to the axis LED-PD1-4 and is identical to the above-mentioned photodiodes which is supplied with an always constant portion of the emitted light amount via a diffuse reflector made of Spectralon.

The distances of the LED to each other are 0.7 mm, wherein the 730 nm-LED is equipped double diagonally at the ends of the LED arrangement to each other. The center of the PD1 is positioned 5 mm from the center point of the four-LED-arrangement, the further PD are arranged at a distance of 3.2 mm to each other and are arranged in a line.

Figure 1:
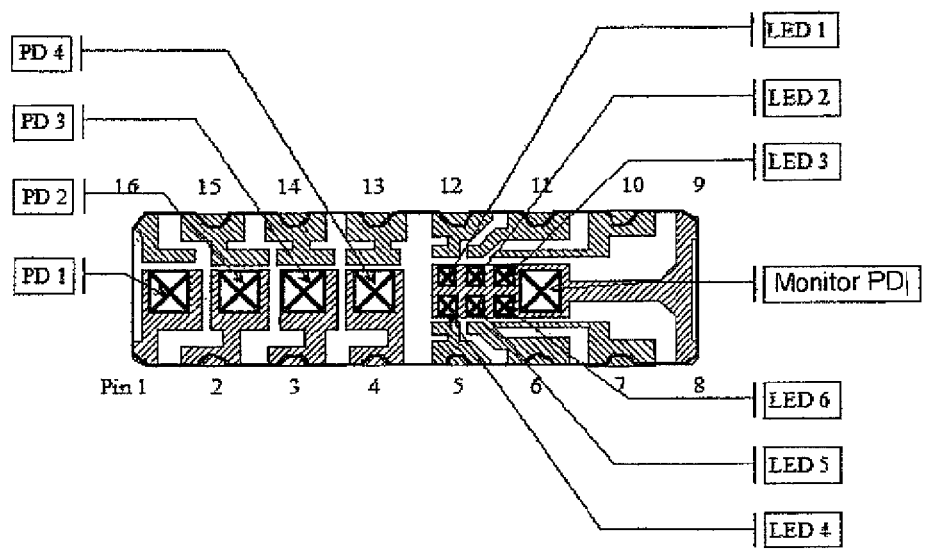
FIG. 1 an exemplary solution of a sensor module with chip-LED
Figure 2:
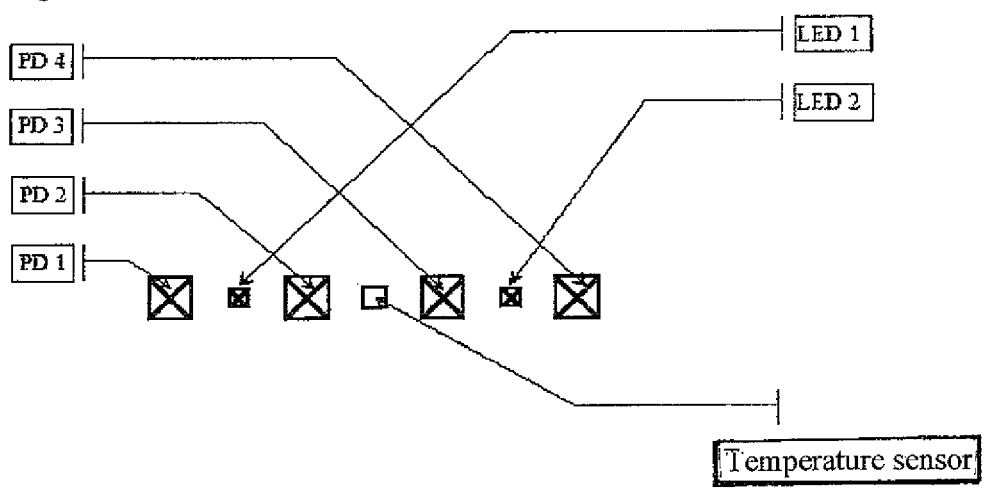
FIG. 2 an exemplary construction of a nested arrangement of a sensor
Figure 3:
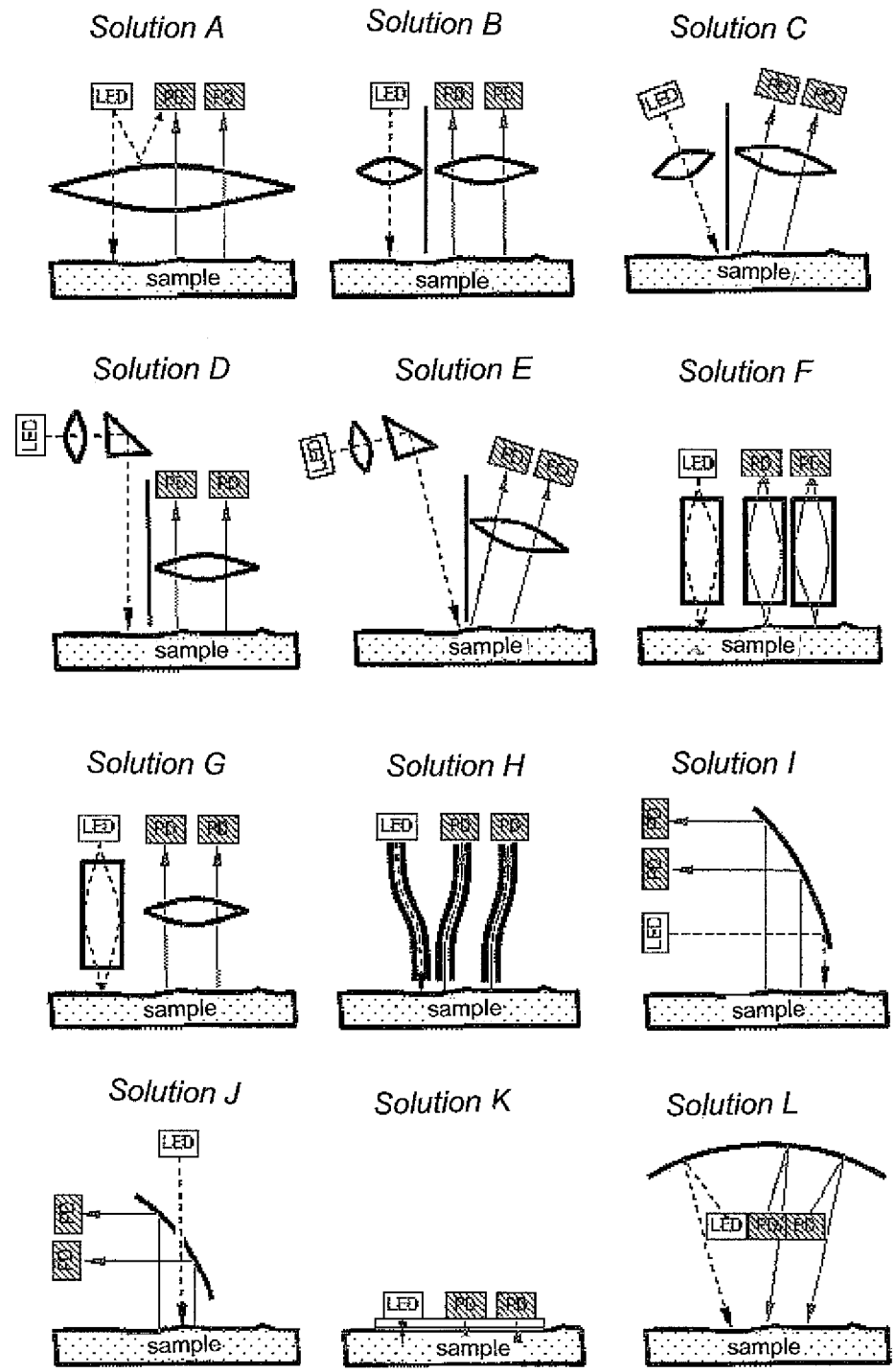
FIG. 3 a solution for optically coupling the sensor with measuring object (sample)
Figure 4:
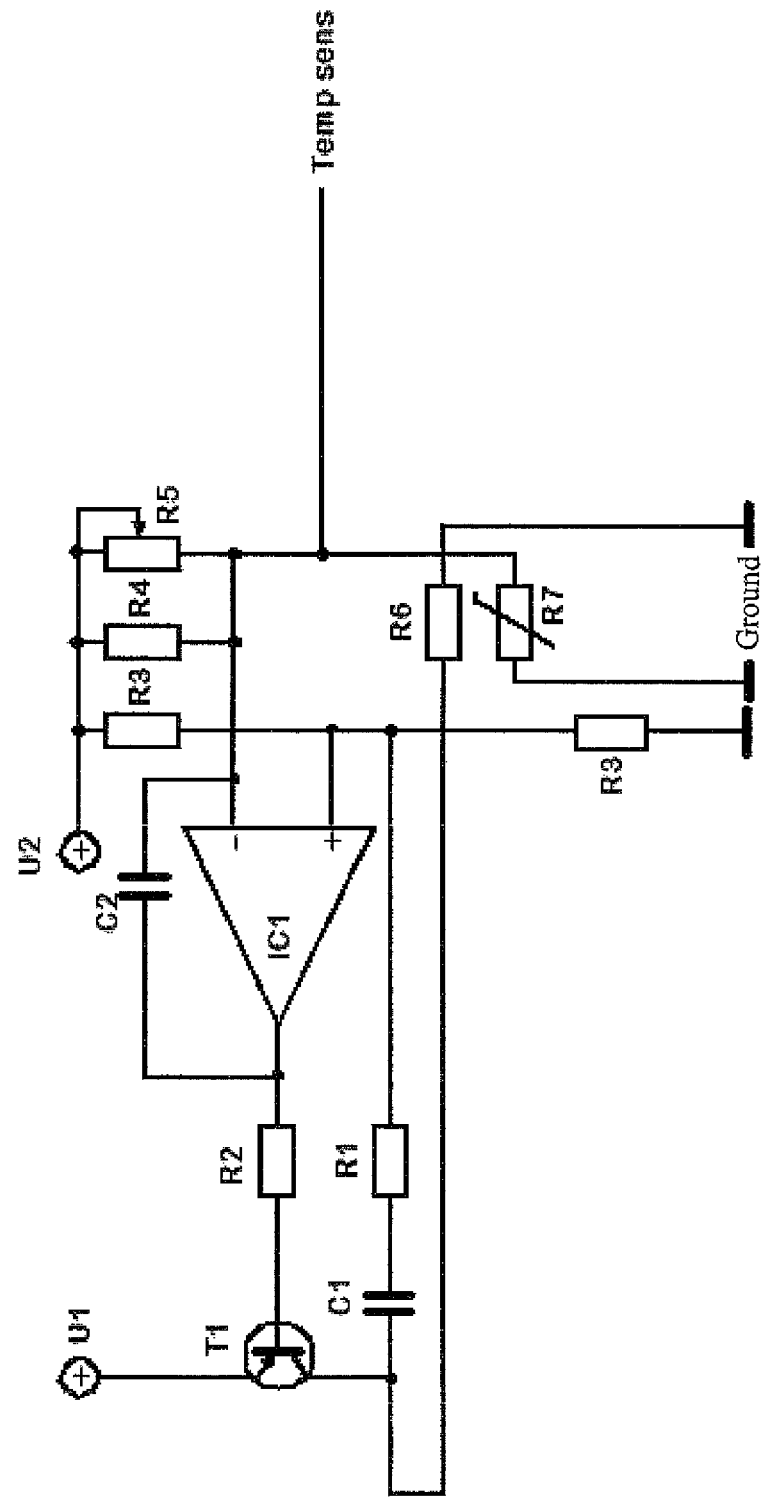
FIG. 4 an exemplary solution of the temperature-stabilization of a component-carrying substrate FIG. 5 an exemplary embodiment antioxidant sensor FIG. 6 an exemplary embodiment water content sensor FIG. 7 an exemplary embodiment for the sensor plate of the hematocrit and oxygen saturation sensor FIG. 8 an exemplary embodiment for the carrier board of the hematocrit and oxygen saturation sensor FIG. 9 an exemplary embodiment meat composition sensor FIG. 10 an exemplary sun protection factor sensor FIG. 11 an exemplary embodiment bilirubin or melanin sensor

At a distance of 0.7 mm adjacent the LED3 and LED4 a temperature sensor is mounted and on the other side of the heat conducting carrier a second temperature sensor is arranged as a wire symmetrically centered below all PD. Below the first temperature sensor and the LED a heating resistor (R6 in FIG. 4) with adjustable current for heating the board is arranged opposite to the components that are situated directly there above and is electrically controlled so as to realize a temperature regulation to the prior-determined maximal ambient temperature. For heat insulation or reduction of the heat conduction the board is provided with slots around the heated components.

The sensor board is mounted on a carrier made of black PEEK (similar coefficient of expansion as the board substance material FR4), in which a walling is formed which protrudes as radiation barrier into a slot formed between LED1 to LED4 and PD1 to PD4. In the carrier a cylindrical bore (with threading for lowering interfering radiation or reflectance in the bore) with diameter M4×0.5 mm is formed symmetrically to the LED1 to LED4 and above each photodiode PD1 to PD4 a bore (with threading for reducing interfering radiation or reflectance in the bore) with diameter M3×0.35 mm is symmetrically formed. Above the photodiodes the bores are closed fluid-tight with a common glass window having a thickness of 0.4 mm and the common bore above the LED are closed fluid tight with a glass window having a thickness of 0.4 mm, wherein the radiation barrier protrudes out of the carrier to the degree so that the two windows are interrupted and rest flush against the barrier.

The sensor board is connected with a signal detection board with separate amplification for each sensor and analog-to digital conversion of the signals as well as with a microprocessor for controlling the signal detection. This board also includes a communication interface, which can be configured as a wireless and cable-based interface according to the state of the art.

The communication and control of the energy supply can also be performed on a separate board and can be electrically connected with the remaining boards.

A different construction of the functional units is also conceivable without departing from the invention. In particular the analog-to-digital conversion can be placed together with the detectors on one board and also the radiation sources and detectors can be placed together on one board.

In the microcontroller a firmware-routine detects the digital signals and logarithmizes the signals. Other data pre-processing steps as described above are also advantageous. By means of a calibration function a prediction for the hematocrit and for the oxygen content of the blood is subsequently outputted via the communication interface. The calibration function consists of two parts, the transfer function (signal transfer function) and the predictive function. The first part, the transfer function (signal transfer function) applies to the respective sensor and is adjusted by a calibration transfer function, which includes the tolerances for the individual sensor and is deduced from a comparative measurement on standards with a calibrated (reference) sensor and the individual sensor. The uncorrected transfer function (signal transfer function) for the sensor type and the calibration transfer function are each present as a matrix (LEDi×PDj) which are each transformed to a corrected transfer function (signal transfer function) by element by element multiplication with a standard signal range.

The second part of the calibration function, the predictive function, determines the prediction of the concentration of the target substance. This second part includes the pre-processing (log) of the values obtained from the transfer function (signal transfer function) and their multiplication with the coefficients from the regression analysis (chemometry), which are summed up and are added with an offset and are calculated to the substance concentration via mathematical operations such as for example square root formation and quadrating.

The measuring site of the sensor is general a blood-filled container, which can have different dimensions and to which the sensor is adjusted by a scattering, light-tight container receptacle.

Meat Composition

Figure 9:
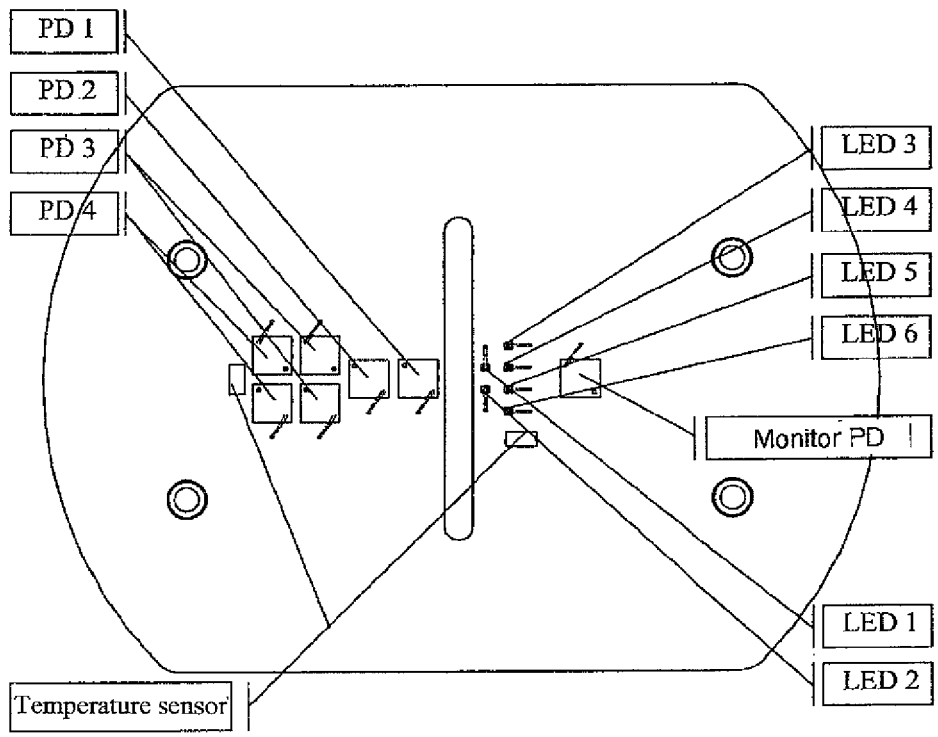

An exemplary embodiment for a sensor for detecting the composition of meat and animal fatty tissue (meat pieces) or of shredded and/or mixed processing products thereof, in particular fat, protein and water content, is described in FIG. 9. The sensor includes six radiation sources each constructed as a Chip-LED with 300 mm side length, with the wavelengths 910 nm, 1200 nm, 1450 nm, 1550 nm, 1680 nm and 1720 nm which respectively ±20 nm tolerance, and six chip-photodiodes made of Indium-Gallium Arsenide (InGaAs) as radiation detectors with 1.000 µm side length with the center distances LED1 to PD1=2.23 mm, LED1 to PD2=3.84 mm, LED1 to PD3=5.45 mm, LED1 to PD4=7.06 mm and a monitor photodiode (monitoring PD) which is arranged at a distance of 2.0 mm to the LED1 but in opposite direction to the other photodiodes and is identical to the above mentioned photodiodes. The photodiodes designated PD3 and PD4 are arranged adjacent each other at a distance of 1.62 mm and are electrically connected in parallel with each other upstream of the amplifier. LED2 is arranged on the sensor board (or also sensor plate) in an axis which is perpendicular to the axis LED1-PD4 at a distance 0.74 mm to LED1. LED3 to LED6 are arranged on an axis, which is parallel to the axis LED1-LED2, which is spaced apart 0.74 mm further from the PDs. Between the LED3 to LED6 a respective distance of 0.74 mm exists.

The LEDs are mounted on a light source board and the photodiodes in a detector board together with a respective temperature sensor in the same surface so that all components are placed on the same side. Both boards are mounted together on a carrier made of a black anodized aluminum alloy, which carrier respectively has a recess of respectively 6×7.8 mm² for light transmittance above the light source board and the detector board, which are closed liquid tight with a transparent window made of glass. Between the windows and the two boards a radiation barrier is formed in the carrier.

The size of the recesses can advantageously be reduced or can also be configured differently corresponding to the principles described in the above description or according to the state of the art so long as the noise does not obscure the signal.

Both boards together form the sensor board, which in turn is connected with a signal transfer board with separate amplification for each sensor and analog-to-digital conversion of the signals, and a further board with a microprocessor for controlling the signal detection. This microprocessor board also includes a communication interface, which can be configured as a wireless and cable-based interface according to the state of the art. The communication and control of the energy supply can also be configured on a separate boards and electrically connected with the remaining boards.

A different construction of the functional units is also conceivable, without departing from the invention. In particular the analog-to-digital conversion can be placed on one board and also the radiation sources and the detectors can be placed on one board.

In the microcontroller a firmware-routine detects the digital signals and logarithmizes the digital signals. Other data pre-processing steps as described above are also advantageous. By means of a calibration function the prediction for the concentration of water, fat and protein in the pieces of meat is outputted via the communication interface. The calibration function consists of two parts, the transfer function (signal transfer function) and the predictive function. The first part, the transfer function (Signal transfer function) applies to the respective sensor and is adjusted by a calibration transfer function, which contains the tolerances for the individual sensor and is deduced from a comparative measurement on standards with a calibrated (reference) sensor and the individual sensor. The uncorrected transfer function (signal transfer function) for the sensor type and the calibration transfer function are each present in the form of a matrix (LEDi×PDj) which are transformed to a corrected transfer function (signal transfer function) by element by element multiplication with a standard signal range.

The second part of the calibration function, the predictive function, determines the prediction of the concentration of the target substance. This second part includes the pre-processing (log) of the values obtained from the transfer function (signal transfer function) and their multiplication with the coefficients of the regression analysis (chemometry), which are summed up and are added with an offset and are calculated to the substance concentrations via mathematical operations such as for example square root formation and quadrating.

The measuring site for the sensor during operation is generally the surface of meat or fatty tissue, wherein cut-off tissue surfaces without fascia cover and with a small curvature or processing products thereof are preferred.

Sun Protection Factor Determination

Figure 10:
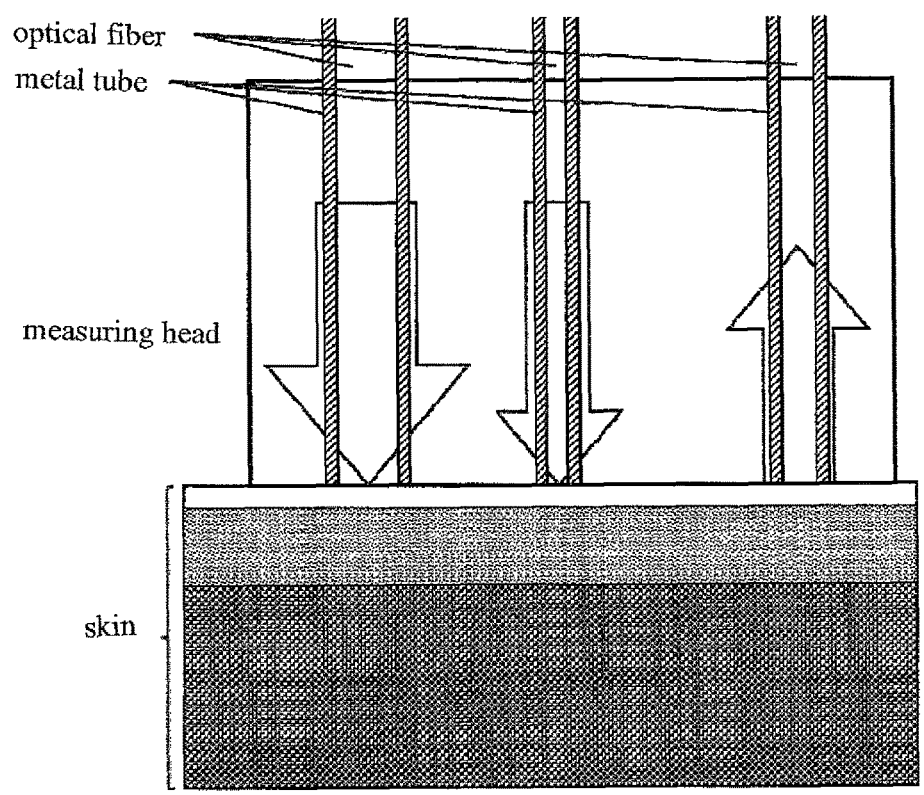

An exemplary embodiment of a sensor for detecting light damping by the uppermost skin layers in the epidermis for determining the light protection of the skin as well as sunscreen products is shown in FIG. 10. The sensor includes a broadband Xenon-light source with light portions in the UVA, UVB and visible and near infrared spectral range, which transmits, interruptible by a first shutter, into a first illumination optical fiber and on the opposite side of the lamp couples light via a second shutter into a second illumination optical fiber. A detection optical fiber is coupled to the entrance slit of a spectrometer for the UVA, UVB, the visible and the near infrared range or the optical fiber represents the entrance slit by virtue of its geometric dimensions. The fiber ends of the two or more illumination optical fibers that is distal to the radiation source or the detector and the at least one detection optical fiber are joint in to form an optical measuring head, which during operation is directly placed with the optical fiber end surfaces on the site of the skin to be measured. The optical fiber for the detection is permeable for the spectral ranges to be tested, the optical fibers for the illumination may be only partially permeable, wherein the losses are compensated by a stronger radiation source. The optical fibers all have a diameter in the range from 50 to 600 µm, which is adjusted to the respectively tested spectral range, with small diameters being used in the case of a small optical penetration depth into the skin, for example in the ultraviolet range, and greater diameters being used in the case of a greater optical penetration depth into the skin, such as for example in the red and near infrared spectral range. The light conductors are arranged in a line, wherein the detection surfaces are arranged so that depending on the diameter of the optical fiber different detection surfaces are generated and due to the arrangement different distances d1 and d2 of the detection optical fiber to the first or the second illumination optical fiber result. The total reflectance in the respective optical fiber represents a first radiation barrier between the optical fibers, the sheath of the optical fiber or metal represents a second radiation barrier, the embedding medium for preparing the optical fiber arrangement represents a third radiation barrier and an additional metal tube about each individual fiber represents a fourth radiation barrier, which is optional.

For conducting a measurement first all shutters are closed and a dark spectrum is measured with the spectrometer, then the shutter 1 is opened and a spectrum for the distance d1 is measured, subsequently the shutter 1 is closed, the shutter 2 is opened and a spectrum for the distance d2 is measured. The spectra d1 and d2 are respectively corrected by subtraction of the dark spectrum and are made available to the analysis. Advantageously the integration time for the spectrometer measurements is adjusted to the respective light amount for the distances d1 and d2 and a respective dark spectrum is separately detected for the at least two different integration times and correctly assigned to the measurements conducted with this integration time respectively subtracted.

The calibration function consists of two parts, the transfer function (signal transfer function) and the predictive function. The first part, the transfer function (signal transfer function), applies to the respective sensor and is adjusted by a calibration transfer function, which includes the tolerances for the individual sensor and is deduced from a comparative measurement on a measurement at standards with a calibrated (reference) sensor and the individual sensor. The uncorrected transfer function (signal transfer function) for the sensor type and the calibration transfer function are present as a matrix (wavelength_i×detection_j) which are transformed to a corrected transfer function (signal transfer function) by element by element multiplication with a standard signal range.

The second part of the calibration function, the predictive function, determines the prediction of a light damping by the skin. This second part includes the preprocessing (log) of the values obtained from the transfer function (signal transfer function) and their multiplication with the coefficients from the regression analysis (chemometry), which are summed up and are added with an offset and are calculated to the light damping via mathematical operations such as square root formation and quadrating.

In a measurement on the skin, a prediction for the intrinsic spectral damping of the skin itself is determined for the measured light damping with the calibration function. When a sunscreen product is subsequently applied to this skin area the spectral sun protection factor can be determined by forming the ratio of the spectral light damping prior to and after the application of the sunscreen product.

By allowing a waiting period to elapse between the two measurements, the influence of the waiting period on the sun protection, for example washing off or rubbing on the clothing or other manipulations, can be determined.

An measurement arrangement alternative to the above measurement arrangement is generated by an illumination optical fiber and two detection optical fibers arranged at a distance d1 and d2 to each other, which are either connected to two spectrometers or to one multichannel spectrometer for separate detection of the two spectra for d1 and d2. The measurement process can hereby be conducted for the distances d1 and d2 simultaneously. The further measurement and analysis is conducted analogously to the above description.

As a further alternative a central single optical fiber and two concentric rings of optical fibers are configured with a distance d1 and d2 about the central optical fiber. The two rings are each either conducted to the light source with two outputs or to the two spectrometers or to the multi-channel spectrometer with two inputs. The further measurement is conducted analogously to the description above.

Bilirubin and Melanin

Figure 11:
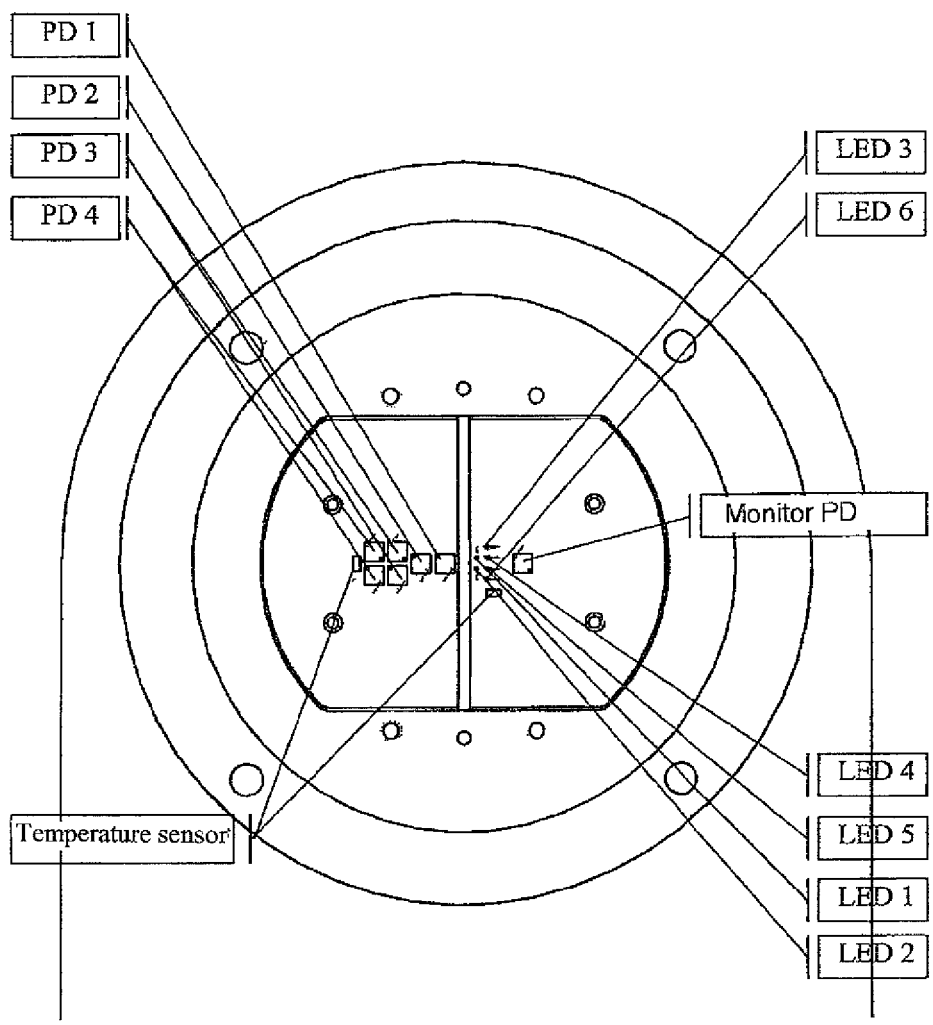

An exemplary embodiment for a sensor for detecting bilirubin in the skin is shown in FIG. 11. The main interfering variables are hemoglobin or blood and melanin. With this the sensor can also be used for determining the melanin content in the skin. The sensor includes six radiation sources each constructed as a chip-LED with 300 µm side length, with the average wavelengths 430 nm, 450 nm, 470 nm, 500 nm, 630 nm 700 nm and four chip-photodiodes made of silicone as radiation detectors with 1.000 µm side length with the average distances LED1 to PD1=2.23 mm, LED1 to PD2=3.84 mm, LED1 to PD3=5.45 mm, LED1 to PD4=7.06 mm and a monitoring photodiode, which is arranged at a distance of 2.6 mm to the LED1 but in opposite direction and is identical to the above-mentioned photodiodes. LED2 is arranged on the sensor board in an axis which is perpendicular to the axis LED1-PD4 at a distance 0.74 mm. LED3 to LED6 are arranged on an axis which is parallel to the axis LED1-LED2, which is located further from the PD by 0.74 mm, between the LED3 to LED6 there is a distance of 0.74 mm.

The selection of the wavelengths can be changed wherein for bilirubin in the blue wavelength range (400-520 nm) at least two wavelengths or wavelength ranges are selected without increased blood absorption and for the melanin correction or measurement a wavelength in the blue wavelength range is sufficient (further roes to be included is advantageous), but on the other hand at least one wavelength in the red spectral range (600-780 nm) without increased blood or water absorption is provided.

The LEDs are mounted on a light source board and the photodiodes on a detector board together with respectively one temperature sensor on the same surface so that all components are arranged on the same side. Both boards are mounted together on a carrier made of a black anodized aluminum alloy, with each carrier having a recess of respectively 6×7.8 mm$^2$ for light transmittance above the light source board and the detector board, and being closed liquid-tight with a transparent window made of glass. Between the windows and the two boards a radiation barrier is provided in the carrier.

The size of the recess can advantageously be decreased or can also be configured differently corresponding to the principles explained above or according to the state of the art which the sensor changing its accuracy, so long as the signal of the detectors is not obscured by noise.

Both boards together form the sensor board, which itself is connected with a signal detection board with a separate amplification for each detector and analog-to-digital conversion of the signals and a further board with a microprocessor for controlling the signal detection. This microprocessor board includes also a communication interface, which can be configured as a wireless and cable based interface according to the state of the art. The communication and control of the energy supply can also be conducted on a separate board and can be electrically connected with the remaining boards.

Another construction of the functional units is conceivable without departing from the scope of the invention. In particular the analog-to-digital conversion can be arranged on one board and also the radiation sources and detectors can be arranged on one board.

In the microcontroller a firmware-routine detects the digital signals and logarithmizes these signals. Other data preprocessing steps such as explained above are also advantageous. By means of a first calibration function a prediction for the bilirubin value and with a second calibration function, which can be implemented in a further sensor or in the same sensor, the concentration for the melanin value in the skin or the corrected concentration is outputted via the communication interface. The calibration function consists of two parts, the transfer function (signal transfer function) and the predictive function. The first part, the transfer function (signal transfer function), applies to the individual sensor and is adjusted by a calibration transfer function, which contains tolerances of the individual sensor and is deduced from a comparative measurement on standards with a calibrated (reference) sensor and the individual sensor. The uncorrected transfer function (signal transfer function) for the sensor type and the calibration transfer function are each present as a matrix (LEDi×PDj), which are transformed to a corrected transfer function (signal transfer function) by element by element multiplication with a standard signal range.

The second part of the calibration function, the predictive function, determines the prediction of the concentration of the target substance and eliminates hereby the influence of the interfering substance or other interfering influences that were present in the measurements. This second part includes the preprocessing (log) of the values obtained from the transfer function (signal transfer function) and their multiplication with the coefficients from the regression analysis (chemometry), which are summed up and are added to an offset and are calculated to the substance concentration via mathematical operations such as square root formation and quadrating.

The measurement site for the sensor during operation is generally the skin, wherein areas without hair and with small curvatures are preferred.

What is claimed is:

1. A spatially resolving optical sensor device, comprising:
multiple radiation sources;
multiple radiation detectors for determining an amount of target substances in strongly scattering measuring objects, said multiple radiation sources being arranged at respective different predetermined distances to the multiple radiation detectors;
a radiation barrier configured to absorb and/or reflect radiation of at least one wavelength range, said radiation barrier separating the multiple radiation sources from the multiple radiation detectors so that the radiations generated by the multiple radiation sources first pass through the measuring object by a path length before reaching the multiple radiation detectors; and
an amplifier configured to amplify signals of the radiation detectors arranged at the different predetermined distances to the radiation sources and separated from the radiation sources by the radiation barrier so that similar signal amplitudes for all of the multiple radiation detectors result.

2. The sensor device of claim 1, wherein the radiation barrier is a substrate which caries components and/or is a housing that surrounds the multiple radiation sources and with this blocks a radiation conduction in the substrate and/or a signal conduction through the housing.

3. The sensor device of claim 1, wherein at least one of the radiation sources is configured and/or arranged so that the radiation passes from the radiation source through the measuring object up to a predetermined depth.

4. The sensor device of claim 1, wherein the distances of at least two of the multiple radiation detectors to the multiple radiation sources are selected so that a path length of the radiation in a target volume containing the target substance to be detected is maximized and measuring volumes for the different radiation detectors at least partially overlap.

5. The sensor device of claim 1, wherein the multiple radiation sources and multiple radiation detectors are arranged so as to result in a depth weighting which reduces an influence of interfering surface-proximate volumes or an influence of volumes located at a deeper depth than the target volume by a calculation of the signals at different distances.

6. The sensor device of claim 1, wherein at least one of the radiation sources is configured to enable irradiation with at least one wavelength or at least one wavelength range for each of an interfering variable, and wherein the multiple sensor devices are configured to detect more than one wavelength or wavelength range thereby increasing a sensitivity for the target substance and/or enabling a resolution of subclasses of the target substance.

7. The sensor device of claim 1, further comprising a temperature adjustment unit configured adapted to heat or cool the multiple radiation sources so that the temperature of the radiation sources is adjustable to a predetermined temperature value.

8. The sensor device of claim 1, wherein the sensor device is configured to perform a measuring series on measuring objects or on a substance mixtures that have similar properties compared to the measuring object with regard to the target substance and interfering variables in which the concentration of the target substance as reference value is varied in a targeted manner or is known by way of a different measuring method performed on different measuring objects and in which interferences can be varied and a calibration instruction can be determined which enables a prediction of the concentration of the target substance and with this the sensor device is available as a reference device with a reference calibration for a subsequent calibration transfer.

9. The sensor device of claim 8, wherein the sensor device has a calibration transfer means and/or can be connected with a calibration transfer means which is configured to transfer the reference calibration to further sensor device of similar construction, in that comparative measurements are preformed with the reference sensor devices and the sensor devices of same construction and a signal transfer function of the sensor devices of same construction can be adjusted when the deviation is excessive.

10. The sensor device of claim 9, wherein the multiple radiation sources comprise radiation sources with little water absorption and with this a higher penetration depth for the subcutis, and radiation sources with a higher water absorption and with this a lower penetration depth for the so as to enable an analysis of a water content by way of wavelength dependent differences of a penetration depth for the dermis and the subcutis separately.

11. The sensor device of claim 1, wherein the sensor device is configured to measure target substances in a skin of a user, said target substances being antioxidants and flavonoids or carotinoids, in particular beta carotin, lykopin, lutein, zeaxanthin or capsanthin, which are to be measured in the epidermis and dermis, or the target substances to be measured are fat, water and protein in animal tissue or meat products, which are either grown or are present after a processing process, or the target substance to be measured is melanin which is to be measured in the epidermis, or the target substance is bilirubin which is to be measured in the skin, or the target substance to be measured in the skin is water which is to be measured in the skin at different concentrations in the epidermis, dermis and the subcutis and in dependence on time is to be evaluated as liquid incorporation in case of heart inefficiency, for an evaluation of a sufficient liquid supply or for an evaluation of a kidney function.

12. The sensor device of claim 1, wherein the sensor device is configured to measure as target substances hemoglobin and/or oxygenated hemoglobin and/or to determine a hematocrit in the blood in an extra corporal blood circulation during dialysis or apheresis of blood or another situation in which a part of the blood is located in a tube system or a cuvette as measuring location.

13. The sensor device of claim 1, wherein the radiation sources and radiation detectors are closed toward the measuring object by a respective window and the radiation barrier arranged between the radiation sources and radiation detectors ends flush with or protrudes over the windows toward the measuring object.

14. The sensor device of claim 13, wherein the sensor device is configured to analyze target substances for different subclasses separately by selecting a respective radiation source for each of the different subclasses so that an average wavelength of the radiation source corresponds to an absorption maximum of a respective one of the different the subclasses of the target substances.

15. The sensor device of claim 13, wherein the sensor device is configured to determine a predictive value of the target substance from the measurement of the target substance, and wherein the sensor device has a communication interface which is connected or connectable with an output device and the communication interface is configured to transfer the predictive value of the target substance to the output device.

16. A spatially resolving optical sensor device, comprising:
   multiple radiation sources;
   multiple radiation detectors for determining an amount of target substances in strongly scattering measuring objects, said multiple radiation sources being arranged at respective different predetermined distances to the multiple radiation detectors, wherein a surface or a number of the multiple radiation detectors is selected so that that similar signal amplitudes for all of the multiple radiation detectors result; and
   a radiation barrier configured to absorb and/or reflect radiation of at least one wavelength range, said radiation barrier separating the multiple radiation sources arranged at respective different predetermined distances to the multiple radiation detectors from the multiple radiation detectors so that the radiations generated by the multiple radiation sources first pass through the measuring object by a path length before reaching the multiple radiation detectors.

* * * * *